US006077832A

United States Patent [19]
Chamberlain et al.

[11] Patent Number: 6,077,832
[45] Date of Patent: *Jun. 20, 2000

[54] ANTIVIRAL BENZIMIDAZOLE NUCLEOSIDE ANALOGUES AND A METHOD FOR THEIR PREPARATION

[75] Inventors: Stanley Dawes Chamberlain; Susan Mary Daluge; George Walter Koszalka, all of Chapel Hill, N.C.

[73] Assignee: Glaxo Wellcome Inc., Five Moore Drive, N.C.

[*] Notice: This patent issued on a continued prosecution application filed under 37 CFR 1.53(d), and is subject to the twenty year patent term provisions of 35 U.S.C. 154(a)(2).

[21] Appl. No.: 08/765,758

[22] PCT Filed: Jul. 6, 1995

[86] PCT No.: PCT/GB95/01597

§ 371 Date: Jan. 6, 1997

§ 102(e) Date: Jan. 6, 1997

[87] PCT Pub. No.: WO96/01833

PCT Pub. Date: Jan. 25, 1996

[30] Foreign Application Priority Data

Jul. 7, 1994 [GB] United Kingdom ............... 9413724

[51] Int. Cl.[7] .................. A61K 31/70; C07H 19/052

[52] U.S. Cl. .................................. 514/43; 536/28.9

[58] Field of Search ......................... 536/28.9; 514/43

[56] References Cited

U.S. PATENT DOCUMENTS

| | | | |
|---|---|---|---|
| 3,399,987 | 9/1968 | Woods et al. | 548/310.4 |
| 3,555,040 | 1/1971 | Frick et al. | 548/310.4 |
| 3,655,901 | 4/1972 | Jensen et al. | 548/310.4 |
| 4,002,623 | 1/1977 | Kadin | 544/132 |
| 5,248,672 | 9/1993 | Townsend et al. | 514/43 |
| 5,360,795 | 11/1994 | Townsend et al. | 514/43 |
| 5,399,580 | 3/1995 | Daluge | 514/394 |
| 5,473,063 | 12/1995 | Classon et al. | 536/122 |
| 5,534,535 | 7/1996 | Townsend et al. | 514/394 |
| 5,574,058 | 11/1996 | Townsend et al. | 514/394 |
| 5,646,125 | 7/1997 | Townsend et al. | 514/43 |
| 5,654,283 | 8/1997 | Townsend et al. | 514/43 |
| 5,665,709 | 9/1997 | Townsend et al. | 514/43 |

FOREIGN PATENT DOCUMENTS

| | | |
|---|---|---|
| 0 136 938 | 4/1985 | European Pat. Off. . |
| 304624 | 3/1989 | European Pat. Off. . |
| 0 350 467 | 1/1990 | European Pat. Off. . |
| 0 515 156 | 11/1992 | European Pat. Off. . |
| 2130 030 | 12/1972 | Germany . |
| 9207867 | 5/1992 | WIPO . |
| 92/18517 | 10/1992 | WIPO . |
| 93/18009 | 9/1993 | WIPO . |
| 9408456 | 4/1994 | WIPO . |
| 9601833 | 1/1996 | WIPO . |

OTHER PUBLICATIONS

Methods of Nucleoside Synthesis. Vorbrueggen, Helmut. Res. Lab., Schering A.-G., Berlin, D–1000/65, Fed. Rep. Ger. NATO Adv. Study Inst. Ser., Ser. A (1979), A26(Nucleoside Analogues: Chem., Biol., Med. Appl.), 35–69.

Vorbrüggen et al., "Nucleoside Synthesis with Trimethylsilyl Triflate and Perchlorate as Catalysts," Chem. Ber. 114, pp. 1234–1255 (1981).

Vorbrüggen et al., "New Catalysts for the Synthesis of Nucleosides," Angew. Chem. Internat. Edit. 14(6), pp. 421–422 (1974).

Gordon et al., "Kinetics of Decay in the Expression of Interferon–Dependent mRNAs Responsible for Resistance to Virus," *Proc. Nat. Acad. Sci. USA* 77(1), 452–456 (Jan. 1980).

Devivar et al., "Benzimidazole Ribonucleosides: Observation of An Unexpected Nitration WHen Performing Non–Aqueous Diazotizations with t–butyl Nitrite," *Biorganic & Medicinal Chem. Letters*, 2(9), 1105–1110 (Sep. 1992).

Tigges et al., "Human CD8+ Herpes Simplex Virus–Specific Cytotoxic T–Lymphocyte Clones Recognize Diverse Viron Protein Antigens," *J. Virology*, 66(3), 1622–1634 (Mar. 1992).

Devivar et al., "Benzimidazole Ribonucleosides: Design, Synthesis, and Antiviral Activity of Certain 2–(Alkylthio-)–and 2–(benzylthio)–5, 6–dichloro–1–(β–D–ribofuranosyl)benzimidazoles," *J. Medicinal Chem.*, 37(18), 2942–2949 (Sep. 2, 1994).

Townsend et al.(VII), "Design Synthesis, and Antiviral Activity of Certain 2,5, 6–Trihalo–1–(β–D–ribofuranosyl)benzimidazoles," *J. Medicinal Chem.*, 38(20), 4098–4105 (Sep. 25, 1995).

Yankulov et al., "The Transcriptional Elongation Inhibitor 5–6–Dichloro–1–β–D–ribofuransylbenzimidazole Inhibits Translation Factor IIH–Associated Protein Kinase," *J. Biol Chem.*, 270(41), 23922–23925 (Oct. 13, 1995).

Nassiri et al., "Comparison of Benzimidazole Nucleosides and Ganciclovir on the In Vitro Prol;iferation and Colony Formation of Human Bone Marrow Progenitor Cells," *British J. Haematology*, 93(2), 273–279 (May 1996).

Gudmundsson et al., "Synthesis and Antiviral Activity of Certain 5'–Modified Analogs of 2,5, 6–Trichloro–1–(β–D–ribofuranosyl)benzimidazole," *J. Medicinal Chem.*, 40(5), 785–793 (Feb. 28, 1997).

Zou et al., "Design, Synthesis, and Antiviral Evaluation of 2–Chloro–5, (List continued on next page.)

*Primary Examiner*—Douglas W. Robinson
*Assistant Examiner*—L. Eric Crane
*Attorney, Agent, or Firm*—Lorie Ann Morgan

[57] ABSTRACT

The present invention relates to benzimidazole derivatives and their use in medical therapy particularly for the treatment or prophylaxis of virus infections such as those caused by herpes viruses. The invention also relates to the preparation of the benzimidazole derivatives and pharmaceutical formulations containing them.

30 Claims, No Drawings

OTHER PUBLICATIONS

6–dihalo–1–(β–D–ribofuranosyl)benzimidazoles as Potential Agents for Human Cytomegalovirus Infections," *J. Medicinal Chem.*, 40(5), 811–818 (Feb. 28, 1997).

*Physician's Desk Reference, 52nd Ed.*, Arky and Sifton (eds.), Medical Economics Co., Montvale, NJ, 1998. only pp. 2452–2454 supplied (see "Cytovene"). Month of publication date is unavailable.

*The Merck Index, 11th Ed.*, Budavari et al. (eds.), Merck & Co., Rahway, NJ, 1989, only p. 682 supplied. Month of publication date is unavailable.

Revankar, G.R. et al., The Synthesis of 2–Chloro–1–(β–D–ribofuranosyl)benzimidazole and Certain Related Derivatives (1), J. Heterocycles, vol. 5, pp. 477–483, 1968 (Aug.).

Revankar, G.R. et al., The Synthesis of 2–Chloro–1–β–D–ribofuranosyl–5,6–dimethylbenzimidazole and Certain Related Derivatives (1), J. Heterocycles, vol. 5, No. 4, pp. 615–620, 1968. (Oct.)

European Patent Office Search Report (Apr. 26, 1996; ref. no. 1263W 94).

European Patent Office Communication (Aug. 6, 1997; ref. no. PB1548/EPw).

Gosselin et al., "Synthesis and biological evaluation of new 5,6–dichlorobenzimidazole nucleoside derivatives", Antiviral Chem. Chemotherapy, vol. 5, pp. 243–256, (1994) (Issue No. 4).

ANTIVIRAL BENZIMIDAZOLE NUCLEOSIDE ANALOGUES AND A METHOD FOR THEIR PREPARATION

This application is filed pursuant to 35 U.S.C. § 371 as a United States National Phase Application of International Application No. PCT/GB95/01597 filed Jul. 6, 1995 which claims priority from GB 9413724.7 filed Jul. 7, 1994.

The present invention relates to benzimidazole derivatives and their use in medical therapy particularly for the treatment or prophylaxis of virus infections such as those caused by herpes viruses. The invention also relates to the preparation of the benzimidazole derivatives and pharmaceutical formulations containing them.

Of the DNA viruses, those of the herpes group are the sources of the most common viral illnesses in man. The group includes herpes simplex virus types 1 and 2 (HSV), varicella zoster virus (VZV), cytomegalovirus (CMV), Epstein-Barr virus (EBV), human herpes virus type 6 (HHV-6) and human herpes virus type 7 (HHV-7). HSV-1 and HSV-2 are some of the most common infectious agents of man. Most of these viruses are able to persist in the host's neural cells; once infected, individuals are at risk of recurrent clinical manifestations of infection which can be both physically and psychologically distressing.

HSV infection is often characterised by extensive and debilitating lesions of the skin, mouth and/or genitals. Primary infections may be subclinical although tend to be more severe than infections in individuals previously exposed to the virus. Ocular infection by HSV can lead to keratitis or cataracts thereby endangering the host's sight. Infection in the new-born, in immnunocompromised patients or penetration of the infection into the central nervous system can prove fatal.

VZV is a herpes virus which causes chickenpox and shingles. Chickenpox is the primary disease produced in a host without immunity, and in young children is usually a mild illness characterised by a vesicular rash and fever. Shingles or zoster is the recurrent form of the disease which occurs in adults who were previously infected with VZV. The clinical manifestations of shingles are characterised by neuralgia and a vesicular skin rash that is unilateral and dermatomal in distribution. Spread of inflammation may lead to paralysis or convulsions. Coma can occur if the meninges become affected. VZV is of serious concern in patients receiving immunosuppressive drugs for transplant purposes or for treatment of malignant neoplasia and is a serious complication of AIDS patients due to their impaired immune system.

In common with other herpes viruses, infection with CMV leads to a lifelong association of virus and host. Congenital infection following infection of the mother during pregnancy may give rise to clinical effects such as death or gross disease (microcephaly, hepatosplenomegaly, jaundice, mental retardation), retinitis leading to blindness or, in less severe forms, failure to thrive, and susceptibility to chest and ear infections. CMV infection in patients who are immunocompromised for example as a result of malignancy, treatment with immunosuppressive drugs following transplantation or infection with Human Immunodeficiency Virus, may give rise to retinitis, pneumonitis, gastrointestinal disorders and neurological diseases.

The main disease caused by EBV is acute or chronic infectious mononucleosis (glandular fever). Examples of other EBV or EBV associated diseases include lymphoproliferative disease which frequently occurs in persons with congenital or acquired cellular immune deficiency, X-linked lymphoproliferative disease which occurs namely in young boys, EBV-associated B-cell tumours, Hodgkin's disease, nasopharyngeal carcinoma, Burkitt lymphoma, non-Hodgkin β-cell lymphoma, thymomas and oral hairy leukoplakia. EBV infections have also been found in association with a variety of epithelial-cell-derived tumours of the upper and lower respiratory tracts including the lung.

HHV-6 has been shown to be a causative agent of infantum subitum in children and of kidney rejection and interstitial pneumonia in kidney and bone marrow transplant patients, respectively, and may be associated with other diseases such as multiple sclerosis. There is also evidence of repression of stem cell counts in bone marrow transplant patients. HHV-7 is of undetermined disease aetiology.

Hepatitis B virus (HBV) is a viral pathogen of worldwide major importance. The virus is aetiologically associated with primary hepatocellular carcinoma and is thought to cause 80% of the world's liver cancer. Clinical effects of infection with HBV range from headache, fever, malaise, nausea, vomiting, anorexia and abdominal pains. Replication of the virus is usually controlled by the immune response, with a course of recovery lasting weeks or months in humans, but infection may be more severe leading to persistent chronic liver disease outlined above.

PCT Patent Specification Nos. WO 92/07867 and WO 94/08456 describe certain antiviral polysubstituted benzimidazole nucleoside analogues including β-D-ribofuranosyl riboside analogues. PCT Patent Specification No. WO 93/18009 describes certain antiviral benzimidazole analogues in which the sugar residue is replaced by a carbocyclic group.

It has now been discovered that certain L-sugar substituted benzimidazole compounds as referred to below, are useful for the treatment or prophylaxis of certain viral infections. According to a first aspect of the present invention, novel compounds of the formula (I) are provided:

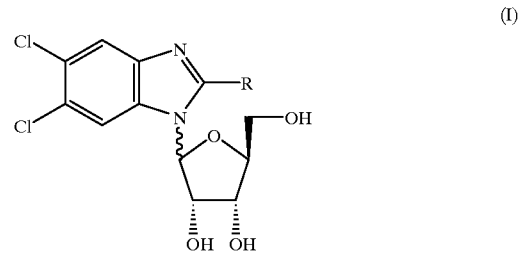

(I)

wherein R represents hydrogen, a halo atom, —NR$^1$R$^2$ where R$^1$ and R$^2$, which may be the same or different, are each independently selected from hydrogen, C$_{1-6}$ alkyl, cyano C$_{1-6}$alkyl, hydroxyC$_{1-6}$alkyl, haloC$_{1-6}$ alkyl, C$_{3-7}$cycloalkyl, C$_{1-6}$alkylC$_{3-7}$cycloalkyl, C$_{2-6}$ alkenyl, C$_{3-7}$cycloalkylC$_{1-6}$alkyl, C$_{2-6}$alkynyl, aryl, arylC$_{1-6}$alkyl, heterocyclicC$_{1-6}$ alkyl, —COC$_{1-6}$alkyl or R$^1$R$^2$ together with the N atom to which they are attached form a 3, 4, 5 or 6 membered heterocyclic ring and pharmaceutically acceptable derivatives thereof.

A further suitable group of compounds of formula (I) is that of formula (Ia)

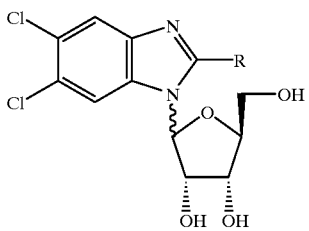

(Ia)

wherein R represents hydrogen or —NR¹R², which may be the same or different, are each independently selected from hydrogen, $C_{1-6}$alkyl, cyano$C_{1-6}$alkyl, hydroxy$C_{1-6}$alkyl, halo$C_{1-6}$alkyl, $C_{3-7}$cycloalkyl, $C_{3-7}$cycloalkyl$C_{1-6}$alkyl, $C_{2-6}$alkenyl, $C_{2-6}$alkynyl, aryl, aryl$C_{1-6}$alkyl, heterocyclic$C_{1-6}$ alkyl, —CO$C_{1-6}$ alkyl (provided that R¹R² are not both hydrogen) or R¹R² together with the N atom to which they are attached form a 3, 4, 5 or 6 membered heterocyclic ring and pharmaceutically acceptable derivatives thereof.

Examples of compounds of formula (I) include the following β anomers of formula (Ib)

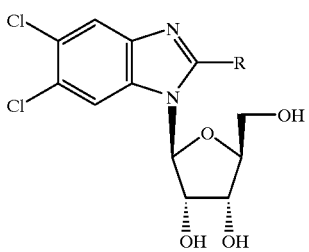

(Ib)

wherein R represents a halo atom or —NR¹R² wherein R¹ represents hydrogen and R² is selected from $C_{1-6}$alkyl, hydroxy$C_{1-6}$alkyl, $C_{3-7}$cycloalkyl, $C_{1-6}$alkyl $C_{3-7}$ cycloalkyl, $C_{2-6}$ alkenyl, $C_{2-6}$ alkynyl, aryl, arylalkyl, or R¹ and R², which may be the same or different, are both $C_{1-6}$ alkyl, or R¹R² together with the N atom to which they are attached form a 3, 4, 5 or 6 membered heterocyclic ring and pharmaceutically acceptable derivatives thereof.

In the alternative, compounds of formula (Ib) are compounds wherein R represents a halo atom or a mono$C_{1-6}$ alkylamino, mono($C_{1-6}$ hydroxyalkyl)amino, di-$C_{1-6}$ alkylamino, $C_{3-7}$cycloalkylamino, $C_{1-6}$alkyl-$C_{3-7}$cycloalkylamino, $C_{2-6}$alkenylamino, $C_{2-6}$ alkynylamino, arylamino, arylalkylamino, or a group of formula —N(CH₂)ₙ, wherein n is 2, 3, 4 or 5 and pharmaceutically acceptable derivatives thereof.

Further examples of compounds of formula (I) above include Examples 1 to 38 as described hereinafter As used herein the term alkyl as a group or part of a group means a straight or branched chain alkyl group. Such alkyl groups preferably have 1–6 carbon atoms, most preferably 1 to 4 and in particular include methyl, ethyl, i-propyl, t-butyl. References to alkenyl groups include groups which may be in the E- or Z- form or a mixture thereof and which when they contain at least three carbon atoms, may be branched. The term halo includes chloro, bromo, fluoro and iodo. The term halo$C_{1-6}$ alkyl means an alkyl group in which one or more hydrogens is replaced by halo and preferably containing one, two or three halo groups. Examples of such groups include trifluoromethyl and fluoroisopropyl. The term aryl as a group or part of a group means phenyl optionally substituted with one or more substituents selected from $C_{1-6}$ alkoxy, (for example methoxy), nitro, halogen, (for example chloro), amino, carboxylate and hydroxy. The term heterocyclic means a saturated or partially saturated (i.e. non-aromatic) 3-,4-,5- or 6- membered ring containing one or more (for example one to four) hetero atoms independently selected from nitrogen, oxygen and sulphur. Examples of such groups include pyrrolidine.

The present invention includes within its scope each possible alpha and beta anomer of the compounds of formula (I) and their physiologically functional derivatives, substantially free of the other anomer, that is to say no more than about 5% w/w of the other anomer, preferably no more than about 2% w/w, in particular less than 1% w/w will be present, and mixtures of such alpha and beta anomers in any proportions. Compounds of formula (I) in the beta anomeric form are preferred.

Preferred compounds of formula (Ib) include those wherein R represents —NR¹R² wherein R¹ represents hydrogen and R² is selected from $C_{1-6}$alkyl, $C_{3-7}$cycloalkyl and halo$C_{1-6}$alkyl and pharmaceutically acceptable derivatives thereof.

Particularly preferred compounds of formula (Ib) include those wherein R represents isopropylarnino, isobutylamino, sec-butylamino, cyclopropylamino, cyclopentylamino and 2-fluoro-1-methylethylamino and pharmaceutically acceptable derivatives thereof.

Compounds of formula (I) having the beta configuration which are of special interest as antiviral agents are 2-cyclopropylamino-5,6-dichloro-1-(β-L-ribofuranosyl)-1H-benzimidazole, 5,6-dichloro-2-((2-fluoro-1-methylethylamino)-1-(β-L-ribofuranosyl)-1H-benzimidazole and 5,6-dichloro-2-isopropylamino-1-(β-L-ribofuranosyl)-1H-benzimidazole and pharmaceutically acceptable derivatives thereof.

The compound 5,6-dichloro-2-isopropylamino-1-(β-L-ribofuranosyl)-1H-benzimidazole has been found to be particularly useful in the treatment of CMV infections.

The compounds of formula (I) including compounds of formula (Ia) and (Ib) above and their pharmaceutically acceptable derivatives are hereinafter referred to as the compounds according to the invention.

By "a pharmaceutically acceptable derivative" is meant any pharmaceutically or pharmacologically acceptable salt, ester or salt of such ester of a compound according to the invention, or any compound which, upon administration to the recipient, is capable of providing (directly or indirectly) a compound according to the invention, or an antivirally active metabolite or residue thereof.

Preferred esters of the compounds according to the invention are independently selected from the following groups: (1) carboxylic acid esters obtained by esterification of the 2'-, 3'- and/or 5'-hydroxy groups, in which the non-carbonyl moiety of the carboxylic acid portion of the ester grouping is selected from straight or branched chain alkyl (for example, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted by, for example, halogen, $C_{1-4}$ alkyl, or $C_{1-4}$ alkoxy or amino); (2) sulphonate esters, such as alkyl- or aralkylsulphonyl (for example, methanesulphonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

In such esters, unless otherwise specified, any alkyl moiety present advantageously contains from 1 to 18 carbon atoms, particularly form 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises a phenyl group.

Preferred carboxylic acid esters according to the present invention include the acetate, butyrate and valerate esters. L-valyl is a particularly preferred amino acid ester.

Any reference to any of the above compounds also includes a reference to a pharmaceutically acceptable salts thereof.

Pharmaceutically acceptable salts include salts of organic carboxylic acids such as ascorbic, acetic, citric, lactic, tartaric, malic, maleic, isethionic, lactobionic, p-aminobenzoic and succinic acids; organic sulphonic acids such as methanesulphonic, ethanesulphonic, benzenesulphonic and p-toluenesulphonic acids and inorganic acids such as hydrochloric, sulphuric, phosphoric, sulphamic and pyrophosphoric acids.

For therapeutic use, salts of the compounds of formula (I) will be pharmaceutically acceptable. However, salts of acids and bases which are non-pharmaceutically acceptable may also find use, for example, in the preparation or purification of a pharmaceutically acceptable compound. All salts, whether or not derived from a pharmaceutically acceptable acid or base, are within the scope of the present invention.

Preferred salts include salts formed from hydrochloric, sulphuric, acetic, succinic, citric and ascorbic acids.

In a further aspect of the invention there are provided the compounds according to the invention for use in medical therapy particularly for the treatment or prophylaxis of viral infections such as herpes viral infections. Compounds of the invention have been shown to be active against CMV infections, although early results suggest that these compounds could also be active against other herpes virus infections such as HSV-1 and -2, HHV 6 and 7, VZV, EBV and HBV infections.

Other viral conditions which may be treated in accordance with the invention have been discussed in the introduction hereinbefore. The compounds of the present invention are particularly suited to the treatment or prophylaxis of CMV infections and associated conditions. Examples of CMV conditions which may be treated in accordance with the invention have been discussed in the introduction hereinbefore.

According to another aspect, the present invention provides a method for the treatment or prevention of the symptoms or effects of a viral infection in an infected animal, for example, a mammal including a human, which comprises treating said animal with a therapeutically effective amount of a compound according to the invention. According to a particular embodiment of this aspect of the invention, the viral infection is a herpes virus infection, such as CMV, HSV-1, HSV-2, VZV, EBV, HHV6 or HHV7. A further aspect of the invention includes a method for the treatment or prevention of the symptoms or effects of an HBV infection.

The present invention further provides a method for the treatment of a clinical condition in an animal, for example, a mammal including a human which clinical condition includes those which have been discussed in the introduction hereinbefore, which comprises treating said animal with a therapeutically effective amount of a compound according to the invention. The present invention also includes a method for the treatment or prophylaxis of any of the aforementioned infections or conditions.

In yet a further aspect, the present invention provides the use of a compound according to the invention in the manufacture of a medicament for the treatment or prophylaxis of any of the above mentioned viral infections or conditions.

The above compounds according to the invention and their pharmaceutically acceptable derivatives may be employed in combination with other therapeutic agents for the treatment of the above infections or conditions. Combination therapies according to the present invention comprise the administration of at least one compound of the formula (I) or a pharmaceutically acceptable derivative thereof and at least one other pharmaceutically active ingredient. The active ingredient(s) and pharmaceutically active agents may be administered simultaneously in either the same or different pharmaceutical formulations or sequentially in any order. The amounts of the active ingredient(s) and pharmaceutically active agent(s) and the relative timings of administration will be selected in order to achieve the desired combined therapeutic effect. Preferably the combination therapy involves the administration of one compound according to the invention and one of the agents mentioned herein below.

Examples of such further therapeutic agents include agents that are effective for the treatment of viral infections or associated conditions such as (1 alpha, 2 beta, 3 alpha)-9-[2,3-bis(hydroxymethyl)cyclobutyl]guanine [(−)BHCG, SQ-34514], oxetanocin-G(3,4-bis-(hydroxymethyl)-2-oxetanosyl]guanine), acyclic nucleosides (e.g. acyclovir, valaciclovir, famciclovir, ganciclovir, penciclovir), acyclic nucleoside phosphonates (e.g. (S)-1-(3-hydroxy-2-phosphonyl-methoxypropyl)cytosine (HPMC), ribonucleotide reductase inhibitors such as 2-acetylpyridine 5-[(2-chloroanilino)thiocarbonyl) thiocarbonohydra-zone, 3'-azido-3'-deoxythymidine, other 2',3'-dideoxynucleosides such as 2',3'-dideoxycytidine, 2',3'-dideoxyadenosine and 2',3'-dideoxyinosine, 2',3'-didehydrothymidine, protease inhibitors such as N-tert-butyl-dehydro-2-[-2(R)-hydroxy-4-phenyl-3(S)-[[N-(2-quinolylcarbonyl)-L-asparginyl]butyl]-(4aS,8aS)-isoquinoline-3(S)-carboxamide (Ro 31-8959), oxathiolane nucleoside analogues such as (−)cis-1-(2-hydroxymethyl)-1,3-oxathiolan-5-yl)-cytosine (3TC) or cis-1-(2-(hydroxymethyl)-1,3-oxathiolan-5-yl)-5-fluoro-cytosine (FTC), 3'-deoxy-3'-fluorothymidine, 5-chloro-2',3-dideoxy-3-fluorouridine, (−)-cis-4-[2-amino-6-(cyclopropylamino)-9H-purin-9-yl]-2-cyclopentene-1-methanol, ribavirin, 9-[4-hydroxy-2-(hydroxymethyl)but-1-yl]-guanine (H2G), tat inhibitors such as 7-chloro-5-(2-pyrryl)-3H-1,4-benzodiazepin-2(H)-one (Ro5-3335), or 7-chloro-1,3-dihydro-5-(1H-pyrrol-2-yl)-3H-1,4-benzodiazepin-2-amine (Ro24-7429), interferons such as α-interferon, renal excretion inhibitors such as probenecid, nucleoside transport inhibitors such as dipyridarnole; pentoxifylline, N-Acetylcysteine (NAC), Procysteine, α-trichosanthin, phosphonoformic acid, as well as immunodulators such as interleukin II or thymosin, granulocyte macrophage colony stimulating factors, erythropoetin, soluble $CD_4$ and genetically engineered derivatives, thereof, or non-nucleoside reverse transcriptase inhibitors such as nevirapine (BI-RG-587), loviride (α-APA) and delavuridine (BHAP), and phosphonoformic acid.

More preferably the combination therapy involves the administration of one of the above mentioned agents and a compound within one of the preferred or particularly preferred sub-groups within formula (I) as described above. Most preferably the combination therapy involves the joint use of one of the above named agents together with one of the compounds of formula (I) specifically named herein.

The present invention further includes the use of a compound according to the invention in the manufacture of a medicament for simultaneous or sequential administration with at least one other therapeutic agent, such as those defined hereinbefore.

The compounds according to the invention, also referred to herein as the active ingredient, may be administered for therapy by any suitable route including oral, rectal, nasal, topical (including transdermal, buccal and sublingual), vaginal and parenteral (including subcutaneous, intramuscular, intravenous, intradermal and intravitreal). It will be appreciated that the preferred route will vary with the condition and age of the recipient, the nature of the infection and the chosen active ingredient.

In general a suitable dose for each of the above-mentioned conditions will be in the range of 0.01 to 250 mg per kilogram body weight of the recipient (e.g. a human) per day, preferably in the range of 0.1 to 100 mg per kilogram body weight per day and most preferably in the range 0.5 to 30 mg per kilogram body weight per day and particularly in the range 1.0 to 20 mg per kilogram body weight per day. (Unless otherwise indicated, all weights of active ingredient are calculated as the parent compound of formula (I); for salts or esters thereof, the weights would be increased proportionally.) The desired dose may be presented as one, two, three, four, five, six or more sub-doses administered at appropriate intervals throughout the day. In some cases the desired dose may be given on alternative days. These sub-doses may be administered in unit dosage forms, for example, containing 10 to 1000 mg or 50 to 500 mg, preferably 20 to 500 mg, and most preferably 100 to 400 mg of active ingredient per unit dosage form.

Ideally, the active ingredient should be administered to achieve peak plasma concentrations of the active compound from about 0.025 to about 100 $\mu$M, preferably about 0.1 to 70 $\mu$M, most preferably about 0.25 to 50 $\mu$M. This may be achieved, for example, by the intravenous injection of a 0.1 to 5% solution of the active ingredient, optionally in saline, or orally administered as a bolus containing about 0.1 to about 250 mg/kg of the active ingredient. Desirable blood levels may be maintained by a continuous infusion to provide about 0.01 to about 5.0 mg/kg/hour or by intermittent infusions containing about 0.4 to about 15 mg/kg of the active ingredient.

While it is possible for the active ingredient to be administered alone it is preferable to present it as a pharmaceutical formulation. The formulations of the present invention comprise at least one active ingredient, as defined above, together with one or more acceptable carriers thereof and optionally other therapeutic agents. Each carrier must be "acceptable" in the sense of being compatible with the other ingredients of the formulation and not injurious to the patient. Formulations include those suitable for oral, rectal, nasal, topical (including transdermal buccal and sublingual), vaginal or parenteral (including subcutaneous, intramuscular, intravenous, intradermal and intravitreal) administration. The formulations may conveniently be presented in unit dosage form and may be prepared by any methods well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then if necessary shaping the product.

The present invention further includes a pharmaceutical formulation as hereinbefore defined wherein a compound of formula (I) or a pharmaceutically acceptable derivative thereof and at least one further therapeutic agent are presented separately from one another and as a kit of parts.

Compositions suitable for transdermal administration may be presented as discrete patches adapted to remain in intimate contact with the epidermis of the recipient for a prolonged period of time. Such patches suitably contain the active compound 1) in an optionally buffered, aqueous solution or 2) dissolved and/or dispersed in an adhesive or 3) dispersed in a polymer. A suitable concentration of the active compound is about 1% to 25%, preferably about 3% to 15%. As one particular possibility, the active compound may be delivered from the patch by electrotransport or iontophoresis as generally described in *Pharmaceutical Research*. 3 (6), 318 (1986).

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricant, inert diluent, preservative, disintegrant (e.g. sodium starch glycollate, cross-linked povidone, cross-linked sodium carboxymethyl cellulose) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredient in a flavoured basis, usually sucrose and acacia or tragacanth; pastilles comprising the active ingredient in an inert basis such as gelatin and glycerine, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

Pharmaceutical formulations suitable for rectal administration wherein the carrier is a solid are most preferably presented as unit dose suppositories. Suitable carriers include cocoa butter and other materials commonly used in the art. The suppositories may be conveniently formed by admixture of the active combination with the softened or melted carrier(s) followed by chilling and shaping in moulds.

Formulations suitable for parenteral administration include aqueous and non-aqueous isotonic sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multidose sealed containers, for example, ampules and vials, and may be stored in a freeze-dried (lyophilized) condition requiring only the addition of the sterile liquid carrier, for example water for injections, immediately prior to use.

Extemporaneous injection solutions and suspensions may be prepared from sterile powders, granules and tablets of the kind previously described.

Preferred unit dosage formulations are those containing a daily dose or unit, daily sub-dose, as herein above recited, or an appropriate fraction thereof, of an active ingredient.

It should be understood that in addition to the ingredients particularly mentioned above the formulations of this invention may include other agents conventional in the art having regard to the type of formulation in question, for example, those suitable for oral administration may include such further agents as sweeteners, thickeners and flavoring agents.

The present invention further includes the following processes, for the preparation of compounds of formula (I) above and derivatives thereof which comprises:

(A) reacting a compound of formula (II)

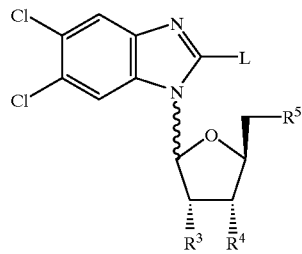

(II)

wherein L is hydrogen and $R^3$, $R^4$ and $R^5$ are each a hydroxy or a protected hydroxy group, with a suitable halogenating agent such as N-bromosuccinamide or when L is a suitable leaving atom or group, for example, a halo atom such as bromine or an organo (for example alkyl) sulphone, or organo (for example alkyl or aralkyl) sulphate such as methylsulphone (MeS(O)$_2$), methylsulphonate (MeS(O)$_2$O) or tosylate (4-MePhS(O)$_2$O) group and $R^3$, $R^4$ and $R^5$ are as hereinbefore defined, with an amine of formula H—NR$^1$R$^2$ (wherein $R^1$ and $R^2$ are as hereinbefore defined); or (B) reacting a compound of formula (III)

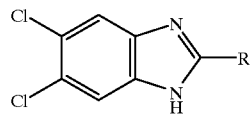

(III)

wherein R is as hereinbefore defined, with a compound of formula (IV)

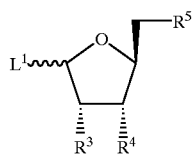

(IV)

wherein $R^3$, $R^4$ and $R^5$ are each a hydroxy or a protected hydroxy group and $L^1$ is a suitable leaving group in the α- or β- position, for example, a halo (for example fluoro, chloro or bromo), an alkyl- or arylthio (for example phenylthio), or an aryl or aliphatic ester group such as benzoate or acetate.

and thereafter or simultaneously therewith effecting one or more of the following further steps may be additionally performed in any desired or necessary order:

(i) removing any remaining protecting group(s);

(ii) converting a compound of formula (I) or a protected form thereof into a further compound of formula (I) or a protected form thereof;

(iii) converting the compound of formula (I) or a protected form thereof into a pharmaceutically acceptable derivative of the compound of formula (I) or a protected form thereof;

(iv) converting a pharmaceutically acceptable derivative of the compound of formula (I) or a protected form thereof into the compound of formula (I) or a protected form thereof;

(v) converting a pharmaceutically acceptable derivative of the compound of formula (I) or a protected form thereof into another pharmaceutically acceptable derivative of the compound of formula (I) or a protected form thereof;

(vi) where necessary, separating the alpha and beta anomers of the compound of formula (I) or of a protected derivative thereof or of a pharmaceutically acceptable derivative of a compound of formula (I)

Process A may conveniently be used for the preparation of a compound of formula (I) wherein R is halogen. Such compounds may conveniently be prepared by reacting a compound of formula (II) wherein L is hydrogen and $R^3$, $R^4$ and $R^5$ are protected hydroxy groups, preferably OC(O)CH$_3$, with a halogenating agent. Halogenation may be effected in a conventional manner, for example, bromination using a brominating agent such as N-bromosuccinimide (NBS) in an aprotic solvent such as THF or preferably 1,4 dioxane heated to 60–150° C., preferably 100° C.

Compounds of formula (I) wherein R is —NR$^1$R$^2$ (wherein $R^1$ and $R^2$ are as hereinbefore defined) may advantageously be prepared from compounds of formula (II) wherein L is a halo atom, such as a bromo or chloro atom. By reaction with an amine H—NR$^1$R$^2$ (wherein $R^1$ and $R^2$ are as hereinbefore defined). The reaction is advantageously effected at an elevated temperature, for example, 70–80° C., in an organic solvent such as ethanol or dimethylsulfoxide.

The protecting groups may be removed by conventional chemical techniques well known to a skilled person.

Compounds of formula (II) wherein $R^3$, $R^4$ and $R^5$ are each a hydroxy group can, for example, be prepared from a corresponding compound of formula (II) wherein $R^3$, $R^4$ and $R^5$ are each a protected hydroxy group. Conventional protecting groups may be used for $R^3$, $R^4$ and $R^5$. Advantageously ester groups such as those described above in relation to the esters of the compounds of formula (I) may be used. These protecting groups may be removed either by conventional chemical techniques such as sodium carbonate in methanol or enzymatically, for example, using pig liver enzyme. Alternatively, $R^3$, $R^4$ and $R^5$ may include silyl protecting groups such as tert-butyldiphenyl-, tert-butyldimethyl-, triisopropyl-silyl groups which may be removed using an appropriate fluoride source, for example HF/Pyridine, n-Bu$_4$NF or Et$_4$NF or a cyclic acetal or ketal such as benzylidene or isopropylidene groups which can be removed under acidic conditions, for example, using tosic acid and methanol.

Alternatively, the compound of formula (II) where $R^3$, $R^4$ and $R^5$ are protected hydroxy groups may be reacted with an agent or under conditions whereby the leaving group L is converted to the desired R group simultaneously with removal of the protecting groups. Examples of such agents include cyclopropylamine and other primary and secondary amines providing that these agents are sufficiently nucleophilic and are not sterically hindered.

Compounds of formula (I) wherein R is as hereinbefore defined and compounds of formula (II) wherein L is as hereinbefore defined may be prepared by reacting a compound of formula (V)

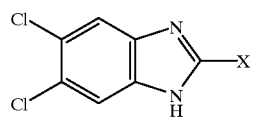

(V)

(wherein X is equivalent to R or L as hereinbefore defined) with a compound of formula (IV)

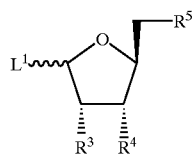

(IV)

(wherein $R^3$, $R^4$ and $R^5$ are each a hydroxy or a protected hydroxy group and $L^1$ is as hereinbefore defined.

The reaction of the compounds of formula (IV) and (V) may be effected using a Lewis acid such as trimethylsilyl triflate, stannic tetrachloride, or boron trifluoride, the former being preferred. The reaction is generally effected in an aprotic solvent and at an elevated temperature, for example, in acetonitrile at 15–30° C. or 1,2-dichloroethane at 70–90° C.

The compound of formula (V) is advantageously trimethylsilylated at the $N_1$-position in the above procedures to improve solubility; for example by treatment with trimethylsilyl chloride, hexamethyl disilazane or, most preferably, N,O-bis-trimethylsilyl acetamide (BSA). This silylation can be effected in a solvent preferably 1,2-dichloroethane or acetonitrile preferably at 70–80°. After completion of the silylation reaction, a Lewis acid may be added followed by addition of the compound of formula (IV).

Compounds of formula (IV) may be prepared by methods well known to a skilled person, for example, in a manner analogous to that known for D-ribose derivatives or by methods readily available from the chemical literature, for example, by methods described in Acton et al. J. Am. Chem. Soc, 1964, 86, 5352. A preferred compound of formula (IV) is the compound wherein $R^3$, $R^4$, $R^5$ and $L^1$ are each OC(O)CH$_3$. This compound may be prepared in an analogous manner to that developed for D-ribose (R. D. Guthrie and S. C. Smith., Chemistry and Industry, 1968, pp 547–548), followed advantageously by recrystallisation from ethanol.

The compounds of formula (V) wherein X is L or a —NR$^1$R$^2$ group (wherein L, R$^1$ and R$^2$ are as hereinbefore defined), may be prepared in accordance with the methods described in PCT specification WO92/07867 incorporated herein by reference.

Alternatively, compounds of formula (V) wherein X is R and R is a group —NR$^1$R$^2$ wherein R$^1$ and R$^2$ are as hereinbefore defined may be prepared by reacting a compound of formula (VI).

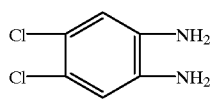

(VI)

with an agent or agents capable of cyclising the diamine into a benzimidazole. Typically compounds of formula (I) may be reacted with an isothiocyanate of formula (VII)

  S=C=NR$^1$R$^2$ (VII)

wherein R$^1$ and R$^2$ are as hereinbefore defined.

The reaction may be carried out in the presence of a carbodiimide such as dicyclohexyl carbodiimide or 1-cyclohexyl-3-(2-morpholinoethyl)carbodiimide metho-p-toluene-sulphonate conveniently in the presence of an aprotic aromatic solvent such as toluene and most preferably pyridine and at an elevated temperature, preferably 75–150° C.

Compounds of formula (V) wherein X is hydrogen may be obtained commercially or alternatively may be prepared by reacting a compound of formula (VI) with formamidine under aqueous acidic conditions, at room temperature to 80° C.

Compounds of formula (VI) and (VII) may be prepared by methods well known to a skilled person or readily available in the chemical literature or obtained commercially.

Esters according to the invention may be prepared by methods well known in the art, for example, a compound of formula (I) may be converted into a pharmaceutically acceptable ester by reaction with an appropriate esterifying agent, for example, an appropriate acid halide or anhydride.

A compound of formula (I) may be converted into a corresponding pharmaceutically acceptable ether of formula (I) by reaction with an appropriate alkylating agent in a conventional manner.

The compounds of formula (I) including esters thereof, may be converted into pharmaceutically acceptable salts thereof in conventional manner, for example by treatment with the appropriate acid. An ester or salt of an ester of formula (I) may be converted into the parent compound, for example, by hydrolysis.

The beta and alpha anomers may be separated and isolated in pure form by silica gel chromatography using a single solvent or a combination of solvents such as 1:20 methanol:dichloromethane.

The present invention further includes the compounds of formula (II) as hereinbefore defined as novel intermediates. Preferred compounds of formula (II) include those wherein L is hydrogen or a halo atom, preferably chloro or bromo, and $R^3$, $R^4$ and $R^5$ are hydroxy or protected hydroxy groups, preferably $OC(O)CH_3$.

Particularly preferred compounds of formula (II) are 2-bromo-5,6-dichloro-1-(2,3,5-tri-O-acetyl-β-L-ribofuranosyl)-1H-benzimidazole and 2-bromo-5,6-dichloro-1-(β-L-ribofuranosyl)-1H-benzimidazole.

The present invention also includes the intermediates of formula (V) wherein X is R and R is a group $—NR^1R^2$ wherein $R^1$ and $R^2$ are as hereinbefore defined with the proviso that $R^1$ and $R^2$ are not both hydrogen or methyl.

Preferred compounds of formula (V) include 2-(cyclopropylamino)-5,6-dichloro-1H-benzimidazole; 5,6-dichloro-2-(isopropylamino)-1H-benzimidazole and 5,6-dichloro-2-(2-fluoro-1-methylethylamino)-1H-benzimidazole.

The following Examples are intended for illustration only and are not intended to limit the scope of the invention in any way. The term 'active ingredient' as used in the Pharmaceutical examples means a compound of formula (I) or a pharmaceutically acceptable derivative thereof. The term also covers a compound of formula (I) or a pharmaceutically acceptable derivative thereof in combination with one or more therapeutic agents.

EXAMPLE 1

2-Bromo-5,6-dichloro-1-(2,3,5-tri-O-acetyl-beta-L-ribofuranosyl)-1H-benzimidazole 2-Bromo-5,6-dichlorobenzimidazole (1.0 g, 3.8 mmol), N,O-bis(trimethylsiyl) acetamide (Aldrich, 0.94 mL, 3.8 mmol), and acetonitrile (Aldrich Sure Seal, 25 mL) were combined and refluxed under nitrogen for 1 h. The solution was cooled to rt and trimethylsilyl triflate (Aldrich, 1.5 mL, 7.6 mmol) was added. After 15 min, solid 1,2,3,5-tetra-O-acetyl-L-ribofuranose (1.2 g, 3.8 mmol), prepared by the method of Guthrie and Smith (Chemistry and Industry, 1968, pp 547–548) except that L-ribose was used as the starting material, was added. The solution was stirred under nitrogen at rt for 18 h, then poured into 10% aqueous sodium bicarbonate (100 mL) and extracted with dichloromethane (2×150 mL). The organic layers were dried with magnesium sulfate (anhyd), filtered, and evaporated. The crude residue was purified on a silica gel column (5×20 cm, 230–400 mesh) with 1:30 acetone : $CH_2Cl_2$ to give 2-bromo-5,6-dichloro-1-(3,4,5-tri-O-acetyl-beta-L-ribofuranosyl)-1H-benzimidazole (1.2 g, 2.2 mmol, 60%); m.p. 142° C.; $[a]^{20}_D$=(+) 87.4 (c=0.5 DMF); UV $l_{max}$ (e) pH=7.0: 298 nm (7,600), 289 (7,400), 254 (8,800); 0.1 N NaOH: 298 nm (7,600), 289 (7,400), 256 (7,300); MS (EI): m/z (rel. intensity) 524 (0.15, M⁺); ¹H NMR (DMSO-d₆) d 8.08 (s, 1H, Ar—H), 8.01 (s, 1H, Ar—H), 6.22 (d, 1H, H-1', J=7.1 Hz), 5.56 (dd, 1H, H-2', J=7.1 Hz, J=7.2 Hz), 5.45 (dd, 1H, H-3', J=7.2 Hz, J=4.5 Hz), 4.55–4.47 (m, 2H, H-4' and 5'), 4.37 (d, 1H, H-5", J=9.7 Hz), 2.15 (s, 3H, OAc), 2.14 (s, 3H, OAc), 2.01 (s, 3H, OAc).

Anal. Calcd. for $C_{18}H_{17}N_2O_7Cl_2Br$: C, 41.25; H, 3.27; N, 5.34. Found: C, 41.16; H, 3.39; N, 5.20.

In addition, a small amount of the alpha anomer (2-bromo-5,6-dichloro-1-(2,3,5-tri-O-acetyl-alpha-L-ribofuranosyl)-1H-benzimidazole) was obtained (0.11 g, 0.22 mmol, 6%); m.p. <65° C.; $[a]^{20}_D$=(−) 206.8 (c=0.5 DMF); MS (AP+): m/z (rel. intensity): 524 (0.8, M⁺); ¹H NMR (DMSO-d₆) d 7.95 (s, 1H, Ar—H), 7.91 (s, 1H, Ar—H), 6.66 (d, 1H, H-1', J=4.2 Hz), 5.68 (t, 1H, H-2', J=4.6 Hz), 5.52 (t, 1H, H-3', J=5.9 Hz), 4.87–4.81 (m, 1H, H-4'), 4.37–4.24 (m, 2H, H-5'), 2.08 (s, 3H, OAc), 2.03 (s, 3H, OAc), 1.51 (s, 3H, OAc).

Anal. Calcd. for $C_{18}H_{17}N_2O_7Cl_2Br$: C, 41.25; H, 3.27; N, 5.34. Found: C, 41.39; H, 3.35; N, 5.29.

EXAMPLE 2

2-Bromo-5,6-dichloro-1-(beta-L-ribofuranosyl)-1H-benzimidazole

Sodium carbonate (0.28 g, 2.65 mmol) and 2-bromo-5,6-dichloro-1-(2,3,5-tri-O-acetyl-beta-L-ribofuranosyl)-1H-benzimidazole (1.39 g, 2.65 mmol) were combined with water (4 mL), methanol (20 mL) and ethanol (20 mL) and stirred at rt for 1.5 h. Acetic acid (0.3 mL, 5.3 mmol) was added and the suspension was concentrated to a solid. Purification of the residue on a silica gel column (2.5×20 cm, 230–400 mesh) with 1:9 ethanol: $CH_2Cl_2$ gave 2-bromo-5,6-dichloro-1-beta-L-ribofuranosyl-1H-benzimidazole as a white amorphous solid (0.79 g, 2.0 mmol, 75%); m.p. 169° C.; $[a]^{20}_D$=(+) 105 (c=0.5 DMF); UV $l_{max}$ (e): pH 7.0: 298 nm (6,700), 289 (6,500), 255 (6,900); 0.1 N NaOH: 298 nm (6,700), 295 (5,400), 256 (6,700); MS (CI): m/z 399 (M+1); ¹H NMR (DMSO-d₆) d 8.57 (s, 1H, Ar—H), 7.96 (s, 1H, Ar—H), 5.89 (d, J=7.9 Hz, H-1'), 5.48 (d, 1H, OH, J=6.3 Hz), 5.42 (t, 1H, OH, J=4.5 Hz), 5.29 (d, 1H, OH, J=4.2 Hz), 4.43 (apparent dd, 1H, H-2', J=13.3 Hz, J=6.1 Hz), 4.14 (apparent t, 1H, H-3', J=4.3 Hz), 4.01 (apparent d, 1H, H-4', J=1.7 Hz), 3.77–3.63 (m, 2H, H-5').

Anal. Calcd. for $C_{12}H_{11}N_2O_4Cl_2Br$. 0.20 $C_2H_6O$: C, 36.57; H, 3.02; N, 6.88. Found: C, 36.68; H, 2.85; N, 7.05.

EXAMPLE 3

2-(Cyclopropylamino)-5,6-dichloro-1-(beta-L-ribofuranosyl)-1H-benzimidazole

Cyclopropylamine (5 mL) and 2-bromo-5,6-dichloro-1-(2,3,5-tri-O-acetyl-beta-L-ribofuranosyl)-1H-benzimidazole (0.10 g, 0.25 mmol) were combined with absolute ethanol (5 mL) and stirred at 75° C. for 24 h. The reaction mixture was concentrated and purified on a silica gel column (2.5 cm×14 cm, 230–400 mesh) with 1:20 methanol:dichloromethane to give 0.073 g of product. This material was further purified on a second silica gel column (2.5 cm×10 cm, 230–400 mesh) with 1:5:5 methanol: ethyl acetate:hexanes to give a white solid (0.051 g, 0.14 mmol, 55%); m.p. 228–230° C. (dec); $[a]^{20}_D$=(−) 17.4 (c=0.5 Ethanol, Abs); UV $l_{max}$ (e): pH 7.0: 303 nm (10,400), 274 (1,700), 259 (9,100); 0.1 N NaOH: 304 nm (10,700), 295 (1,900), 259 (8,800); MS (CI): m/z (rel. intensity) 374 (13.2, M+1); ¹H NMR (DMSO-d₆) d 7.6 (s, 1H, Ar—H), 7.42 (s, 1H, Ar—H), 5.71 (d, 1H, J=7.6 Hz, H-1'), 5.65 (t, 1H, OH, J=4.3 Hz), 5.25–5.21 (m, 2H, OH), 4.22 (apparent dd, 1H, H-2', J=13.4 Hz, J=7.6 Hz), 4.02 (apparent t, 1H, H-3', J=7.1 Hz), 3.95 (s, 1H, H-4'), 3.67–3.62 (m, 2H, H-5'), 2.78–2.74 (m, 1H, cyclopropyl-CH), 0.67 (d, 2H, J=7.1 Hz, cyclopropyl-$CH_2$), 0.53–0.47 (m, 2H, cyclopropyl-$CH_2$).

Anal. Calcd. for $C_{15}H_{16}N_3O_4Cl_2$. 0.50 $C_4H_8O_2$. 0.15 $C_6H_{14}$: C, 49.98; H, 5.18; N, 9.77. Found: C, 49.86; H, 5.18; N, 9.80.

EXAMPLE 4

2-(Allylamino)-5,6-dichloro-1-(beta-L-ribofuranosyl)-1H-benzimidazole

Allylamine (5 mL) and 2-bromo-5,6-dichloro-1-(2,3,5-tri-O-acetyl-beta-L-ribofuranosyl)-1H-benzimidazole (0.60 g, 1.14 mmol) were combined with absolute ethanol (10 mL) and stirred at 75° C. for 24 h. The reaction mixture was concentrated and purified on a silica gel column (2.5 cm×20 cm, 230–400 mesh) with 1:9 methanol:dichloromethane to give a off white solid (0.325 g, 0.87 mmol, 76%); m.p. 220° C. (dec); $[a]^{20}{}_D$=(−) 16.0 (c=0.5 DMF); UV $l_{max}$ (e): pH 7.0: 303 nm (11,200), 275 (2,000), 259 (9,900); 0.1 N NaOH: 304 nm (11,300), 275 (2,000),259 (9,200); MS (CI): m/z (rel. intensity) 374 (100, M+1); $^1$H NMR (DMSO-d$_6$) d 7.66 (s, 1H, Ar—H), 7.35 (s, 1H, Ar—H), 5.98–5.85 (m, 1H, CH=CH$_2$), 5.76 (d, 1H, J=7.6 Hz, H-1'), 5.62 (t, 1H, OH, J=4.3 Hz), 5.28 (d, 1H, OH, J=7.6 Hz), 5.23 (d, 1H, OH, J=4.2 Hz), 5.16 (d, 1H, CH=CH$_2$, J=18.6 Hz), 5.05 (d, 1H, CH=CH$_2$, J=10.2 Hz), 4.30 (apparent dd, 1H, H-2', J=13.1 Hz, J=7.6 Hz), 4.06 (apparent t, 1H, H-3', J=5.6 Hz), 3.97 (br. s, 1H, H-4', CH$_2$CH=CH$_2$), 3.71–3.60 (m, 2H, H-5').

Anal. Calcd. for $C_{15}H_{17}N_3O_4Cl_2$. 0.30 H$_2$O: C, 47.46; H, 4.67; N, 11.07. Found: C, 47.50; H, 4.68; N, 11.02.

EXAMPLE 5

5,6-Dichloro-2-(isopropylamino)-1-(beta-L-ribofuranosyl)-1H-benzimidazole

Isopropylamine (10 mL) and 2-bromo-5,6-dichloro-1-(2,3,5-tri-O-acetyl-beta-L-ribofuranosyl)-1H-benzimidazole (1.0 g, 1.9 mmol) were combined with absolute ethanol (20 mL) and stirred at 75° C. for 48 h. The reaction mixture was concentrated and purified on a silica gel column (2.5 cm×16 cm, 230–400 mesh) with 1:20 methanol:dichloromethane to give product contaminated with a small amount of higher R$_f$ material. This was repurified on a chromatotron, fitted with a 2 mm silica gel rotor, with 1:25 methanol:dichloromethane to give a white solid (0.43 g, 1.15 mmol, 60%); $[a]^{20}{}_D$=(−) 22.4 (c=0.5 DMF); UV $l_{max}$ (e): pH 7.0: 304 nm (9,500), 275 (1,800), 260 (8,300); 0.1 N NaOH: 304 nm (9,900), 275 (1,900), 260 (8,100); MS (CI): m/z (rel. intensity) 376 (100, M+1); $^1$H NMR (DMSO-d$_6$) d 7.59 (s, 1H, Ar—H), 7.35 (s, 1H, Ar—H), 6.90 (d, 1H, NH, J=7.8 Hz), 5.73 (d, 1H, H-1', J=6.5 Hz), 5.62 (t, 1H, OH, J=4.2 Hz), 5.27–5.23 (m, 2H, OH), 4.27 (apparent dd, 1H, J=13.4 Hz, J=7.6 Hz), 4.11–3.99 (m, 2H), 3.97 (br. s, 1H), 3.72–3.61 (m, 2H, H-5'), 1.18 (d, 6H, CH(CH$_3$)$_2$, J=6.6 Hz).

Anal. Calcd. for $C_{15}H_{19}N_3O_4Cl_2$. 1.00 H$_2$O: C, 45.70; H, 5.37; N, 10.66. Found: C, 45.75; H, 4.98; N, 10.50.

EXAMPLE 6

2-(Cyclopentylamino)-5,6-dichloro-1-(beta-L-ribofuranosyl)-1H-benzimidazole

Cyclopentylamino (5 mL) and 2-bromo-5,6-dichloro-1-(2,3,5-tri-O-acetyl-beta-L-ribofuranosyl)-1H-benzimidazole (0.6 g, 1.1 mmol) were combined with absolute ethanol (10 mL) and stirred at 70° C. for 24 h. The reaction mixture was concentrated and purified on a silica gel column (2.5 cm×16 cm, 230–400 mesh) with 1:9 ethanol:dichloromethane to give a white solid (0.27 g, 0.68 mmol, 59%); m.p. 140° C.; $[a]^{20}{}_D$=(−) 24.0 (c=0.5 DMF) UV $l_{max}$ (e): pH7.0: 305 nm (12,700), 276 (2,400), 260(10,600), 245(7400); 0.1 N NaOH: 305 nm (12,600), 276 (2,200),260 (9,900), 247 (7,300); MS (CI): m/z (rel. intensity) 402 (100 , M+1); $^1$H NMR (DMSO-d$_6$) d 7.60 (s, 1H, Ar—H ), 7.36 (s, 1H, Ar—H), 6.91 (d, 1H, NH, J=6.8 Hz), 5.74 (d, 1H, H-1', J=7.6 Hz), 5.61 (t, 1H, OH, J=4.2 Hz), 5.26 (d, 1H, OH, J=8.1 Hz), 5.23 (d, 1H, OH, J=5.5 Hz), 430–4.14 (m, 2H, NHCH, H-2'), 4.05 (apparent t, 1H, H-3', J=4.9 Hz), 3.96 (br. s, 1H, H-4'), 3.72–3.59 (m, 2H, H-5'), 1.91 (br. s, 2H, CH$_2$), 1.66 (br. s, 2H, CH$_2$), 1.52 (br. s, 4H, CH$_2$).

Anal. Calcd. for $C_{17}H_{21}N_3O_4Cl_2$. 0.20 H$_2$O: C, 50.31; H, 5.31; N, 10.38. Found: C, 50.13; H, 5.31; N, 10.05.

EXAMPLE 7

2-(Benzylamino)-5,6-dichloro-1-r(beta-L-ribofuranosyl)-1H-benzimidazole

Benzylamine (10 mL) and 2-bromo-5,6-dichloro-1-(2,3,5-tri-O-acetyl-beta-L-ribofuranosyl)-1H-benzimidazole (1.0 g, 1.9 mmol) were combined with absolute ethanol (20 mL) and stirred at 70° C. for 24 h. The reaction mixture was concentrated and purified on a silica gel column (2.5 cm×16 cm, 230–400 mesh) with 1:9 ethanol:dichloromethane. The crude product contained benzylamine. This material was further purified on a second silica gel column (2.5 cm×16 cm, 230–400 mesh) with 3:7 acetone:hexanes to give product with a small amount of impurity. A third silica gel column, identical to the second was used for final purification to give an off white solid (0.26 g, 0.62 mmol, 32%); m.p. 123° C.; $[a]^{20}{}_D$=(−) 4.6 (c=0.5 DMF); UV $l_{max}$ (e): pH 7.0: 304 nm (10,600), 276 (1,800), 260 (9,600); 0.1 N NaOH: 305 nm (10,500), 276 (1,500), 260 (8,500); MS (CI): m/z (rel. intensity) 424 (100, M+1); $^1$H NMR (DMSO-d$_6$) d 7.78 (t, 1H, J=5.9 Hz, NH), 7.68 (s, 1H, Ar—H), 7.34 (s, 1H, Ar—H), 7.34–7.18 (m, 5H, Ar—H), 5.80 (d, 1H, H-1', J=7.6 Hz), 5.67 (t, 1H, OH, J=4.1 Hz), 5.32 (d, 1H, OH, J=7.6 Hz), 5.25 (d, 1H, OH, J=4.6 Hz), 4.55 (d, 2H, PhCH$_2$, J=5.7 Hz), 4.34 (apparent dd, 1H, H-2', J=13.1 Hz, J=7.4 Hz), 4.08 (apparent t, 1H, H-3', J=3.8 Hz), 4.00 (br. s, 1H, H-4'), 3.73–3.61 (m, 2H, H-5').

Anal. Calcd. for $C_{19}H_{19}N_3O_4Cl_2$. 0.10 H$_2$O: C, 53.56; H, 4.54; N, 9.86. Found: C, 53.23; H, 4.62; N, 9.71.

EXAMPLE 8

2-Azetidino-5,6-dichloro-1-(beta-L-ribofuranosyl)-1H-benzimidazole

Azetidine (1 g) and 2-bromo-5,6-dichloro-1-(2,3,5-tri-O-acetyl-beta-L-ribofuranosyl)-1H-benzimidazole (0.6 g, 1.1 mmol) were combined with absolute ethanol (10 mL) and stirred at 75° C. for 72 h. The reaction mixture was concentrated and purified on a silica gel column (2.5 cm×16 cm, 230–400 mesh) with 1:20 methanol:dichloromethane to give an off white solid (0.35 g, 0.93 mmol, 82%); m.p. 244–245° C.; $[a]^{20}{}_D$=(+)69.6 (c=0.5 DMF); UV $l_{max}$ (e): pH 7.0: 305 mn (9,900), 275 (1,500), 260 (9,800); 0.1 N NAOH: 305 nm (9,800), 276 (1,600), 260 (7,800); MS (CI): m/z (rel. intensity) 376 (100, M+1); $^1$H NMR (DMSO-d$_6$) d 8.60 (s, 1H, Ar—H), 7.49 (s, 1H, Ar—H), 5.43 (d, 1H, H-1', J=7.6 Hz), 5.33 (d, 1H, OH, J=6.6 Hz), 5.26 (t, 1H, OH, J=4.7 Hz), 5.13 (d, 1H, OH, J=4.7 Hz), 4.35 (apparent dd, 1H, H-2', J=12.6 Hz, J=6.0 Hz), 4.17 (t, 4H, CH$_2$, J=7.6 Hz), 4.07 (apparent t, 1H, H-3', J=6.1 Hz), 3.88 (d, 1H, H-4', J=2.4 Hz), 3.64 (br. s, 2H, H-5'), 2.39–2.29 (m, 2H, CH$_2$).

Anal. Calcd. for $C_{15}H_{17}N_3O_4Cl_2$: C, 48.14; H, 4.58; N, 11.23. Found: C, 48.00; H, 4.59; N, 11.15.

EXAMPLE 9

5,6-Dichloro-2-(propargylamino)-1-(beta-L-ribofuranosyl)-1H-benzimidazole

Propargylamine (4 mL) and 2-bromo-5,6-dichloro-1-(2,3,5-tri-O-acetyl-beta-L-ribofuranosyl)-1H-benzimidazole (0.6 g, 1.1 mmol) were combined with absolute ethanol (10 mL) and stirred at 70° C. for 4 h. The reaction mixture was concentrated and purified on a silica gel column (2.5 cm×16 cm, 230–400 mesh) with 1:20 ethanol:dichloromethane to give 0.18 g of crude product. This material was further purified on a chromatotron, fitted with a 2 mm rotor, using 1:9 methanol:dichloromethane to give a light yellow solid (0.135 g, 0.36 mmol, 32%); m.p. 182–184° C.; $[a]^{20}{}_D$=(−) 9.2 (c=0.5 DMF); UV $l_{max}$ (e): pH 7.0: 300 nm (8,900), 272 (1,700), 258 (8,300); 0.1 N NaOH: 301 nm (8,700), 272 (1,800), 259 (7,500); MS (CI): m/z (rel. intensity) 372 (100, M+1); $^1$H NMR (DMSO-$d_6$) d 7.73 (s, 1H, Ar—H), 7.58 (t, 1H, J=5.5 Hz, NH), 7.43 (s, 1H, Ar—H), 5.75 (d, 1H, H-1', J=5.0 Hz), 5.66 (t, 1H, OH, J=4.3 Hz), 5.29 (d, 1H, OH, J=7.6 Hz), 5.24 (d, 1H, OH, J=4.2 Hz), 4.28 (apparent dd, 1H, H-2', J=13.2 Hz, J=7.4 Hz), 4.11–4.04 (m, 3H, H-3', C$\underline{H}_2$), 3.97 (br. s, 1H, H-4'), 3.73–3.61 (m, 2H, H-5'), 3.10 (s, 1H, C$\underline{H}$).

Anal. Calcd. for $C_{15}H_{15}N_3O_4Cl_2$. 0.75 $H_2O$: C, 46.71; H, 4.31; N, 10.89. Found: C, 46.52; H, 4.23; N, 10.72.

EXAMPLE 10

5,6-Dichloro-2-(n-propylamino)-1-(beta-L-ribofuranosyl)-1H-benzimidazole

Propylamine (7 mL) and 2-bromo-5,6-dichloro-1-(2,3,5-tri-O-acetyl-beta-L-ribofuranosyl)-1H-benzimidazole (0.6 g, 1.1 mmol) were combined with absolute ethanol (10 mL) and stirred at 70° C. for 24 h. The reaction mixture was concentrated and purified on a silica gel column (2.5 cm×16 cm, 230–400 mesh) with 1:9 ethanol:dichloromethane to give an off white solid (0.36 g, 0.96 mmol, 84%); m.p. 231–233° C.; $[a]^{20}{}_D$=(−) 23.6 (c=0.5 DMF); UV $l_{max}$ (e): pH 7.0: 305 nm (9,900), 275 (1,500), 260 (9,800); 0.1 N NaOH: 305 nm (9,800), 276 (1,600), 260 (7,800; MS (CI): m/z (rel. intensity) 376 (100, M+1); $^1$H NMR (DMSO-$d_6$) d 7.60 (s, 1H, Ar—H), 7.35 (s, 1H, Ar—H), 7.15 (t, 1H, J=5.4 Hz, NH), 5.74 (d, 1H, H-1', J=7.6 Hz), 5.66 (t, 1H, OH, J=4.0 Hz), 5.28 (d, 1H, OH, J=7.6 Hz), 5.24 (d, 1H, OH, J=4.2 Hz), 4.34–4.25 (m, 1H, H-2'), 4.06 (apparent t, 1H, H-3', J=4.7 Hz), 4.00 (br. s, 1H, H-4'), 3.72–3.61 (m, 2H, H-5'), 3.31–3.24 (m, 2H, NH$_2$C$\underline{H}_2$), 1.57 (q, 2H, J=7.3 Hz, $CH_2$), 0.88 (t, 3H, J=7.5 Hz, $CH_3$).

Anal. Calcd. for $C_{15}H_{19}N_3O_4Cl_2$. 0.25 $H_2O$: C, 47.32; H, 5.16; N, 11.04. Found: C, 47.43; H, 5.20; N, 10.74.

EXAMPLE 11

5,6-Dichloro-2-(isobutylamino)-1-(beta-L-ribofuranosyl)-1H-benzimidazole

Isobutylamine (10 ml) and 2-bromo-5,6-dichloro-1-(2,3,5-tri-O-acetyl-beta-L-ribofuranosyl)-1H-benzimidazole (0.6 g, 1.1 mmol) were combined with absolute ethanol (50 mL) and stirred at 75° C. for 24 h. The reaction mixture was concentrated and purified on a silica gel column (2.5 cm×16 cm, 230–400 mesh) with 1:20 methanol:dichloromethane (500 mL), then 1:9 methanol:dichloromethane to give a tan solid (0.39 g, 1.0 mmol. 90%); m.p. 136° C.; $[a]^{20}{}_D$=(−) 28.4 (c=0.5 DMF).

Anal. Calcd. for $C_{16}H_{21}N_3O_4Cl_2$: C, 48.13; H, 5.55; N, 10.52. Found: C, 48.08; H, 5.57; N, 10.41.

EXAMPLE 12

2-((5,6-Dichloro-1-(beta-L-ribofuranosyl)-1H-benzimidazol-2-yl)amino)ethanol Ethanolamine (25 ml) and 2-bromo-5,6-dichloro-1-(2,3,5-tri-O-acetyl-beta-L-ribofuranosyl)-1H-benzimidazole (0.62 g, 1.2 mmol) were combined with absolute ethanol (50 mL) and stirred at 80° C. for 24 h. The reaction mixture was concentrated and purified on a silica gel column (2.5 cm×16 cm, 230–400 mesh) with 1:20 methanol:dichloromethane (500 mL), then 1:9 methanol:dichloromethane. Crude product was obtained which was further purified on a silica gel filter pad with 1:1 acetone: dichloromethane and then with 1:2 ethanol:dichloromethane. Further purification on a chromatotron fitted with a 2 mm rotor, using 1:6 ethanol: ethyl acetate provided pure product (0.064 g, 0.17 mmol, 14%); $[a]^{20}{}_D$=(−) 14.2 (c=0.5 DMF).

Anal. Calcd. for $C_{14}H_{17}N_3O_5Cl_2$. 0.50 $H_2O$: C, 43.43; H, 4.69; N, 10.85. Found: C, 43.74; H, 5.02; N, 10.53.

EXAMPLE 13

5,6-Dichloro-2-((1-ethylpropyl)amino)-1-(beta-L-ribofuranosyl)-1H-benzimidazole 1-Ethylpropylamine (5 ml) and 2-bromo-5,6-dichloro-1-(2,3,5-tri-O-acetyl-beta-L-ribofuranosyl)-1H-benzimidazole (0.6 g, 1.1 mmol) were combined with absolute ethanol (20 mL) and stirred at 80° C. for 24 h. The reaction mixture was concentrated and purified on a silica gel column (2.5 cm×16 cm, 230–400 mesh) with 1:15 methanol:dichloromethane to give product (0.31 g) with a small amount of impurity. This material was further purified on a chromatotron, fitted with a 2 mm rotor, using 1:2 acetone:dichloromethane to give a white solid (0.24 g, 0.59 mmol, 52%); $[a]^{20}{}_D$=(−) 39.4 (c=0.5 DMF).

Anal. Calcd. for $C_{17}H_{23}N_3O_4Cl_2$: C, 50.50; H, 5.73; N, 10.39. Found: C, 50.44; H, 5.88; N, 10.14.

EXAMPLE 14

2-(Cyclohexylamino)-5,6-dichloro-1-(beta-L-ribofuranosyl)-1H-benzimidazole

Cyclohexylamine (5 ml) and 2-bromo-5,6-dichloro-1-(2,3,5-tri-O-acetyl-beta-L-ribofuranosyl)-1H-benzimidazole (0.6 g, 1.1 mmol) were combined with absolute ethanol (20 mL) and stirred at 80° C. for 24 h. The reaction mixture was concentrated and purified on a silica gel column (2.5 cm×16 cm, 230–400 mesh) with 1:15 methanol:dichloromethane to give product (0.38 g) with a small amount of impurity. This material was further purified on a chromatotron, fitted with a 2 mm rotor, using 1:2 acetone:dichloromethane to give, in addition to 0.25 g of slightly impure material, pure product as a white solid (0.059 g, 0.14 mmol, 12%); $[a]^{20}{}_D$=(−) 24.0 (c=0.5 DMF).

Anal. Calcd. for $C_{18}H_{23}N_3O_4Cl_2$. 0.30 $H_2O$: C, 51.27; H, 5.64; N, 9.96. Found: C, 51.18; H, 5.68; N, 9.88.

EXAMPLE 15

2-Anilino-5,6-dichloro-1-(beta-L-ribofuranosyl)-1H-benzimidazole

Aniline (5 ml) and 2-bromo-5,6-dichloro-1-(2,3,5-tri-O-acetyl-beta-L-ribofuranosyl)-1H-benzimidazole (0.6 g, 1.1 mmol) were combined with absolute ethanol (35 mL) and stirred at 80° C. for 14 days. The reaction mixture was concentrated and the aniline was distilled off under high vacuum at 80° C. The brown residue was dissolved in methanol (50 mL) and $K_2CO_3$ was added. This solution was stirred for 18 h. The solution was filtered, concentrated and purified on a silica gel column (2.5 cm×16 cm, 230–400 mesh) with 1:15 methanol:dichloromethane to give a white solid (0.024 g, 0.06 mmol, 5%). MS (AP+): m/z (rel. intensity) 410 (19.39, M+1); $^1$H NMR (DMSO-$d_6$) d 9.09 (s, 1H, NH), 7.83 (s, 1H, Ar—H), 7.78 (d, 1H, Ar—H, J=7.9 Hz), 7.58 (s, 2H, Ar—H), 7.31 (t, 2H, Ar—H, J=7.9 Hz), 6.99 (t, 1H, Ar—H, J=7.5 Hz), 5.95 (d, 1H, H-1', J=7.8 Hz), 5.86 (t, 1H, OH, J=4.4 Hz), 5.38 (d, 1H, OH, J=7.6 Hz), 5.30 (d, 1H, OH, J=4.2 Hz), 4.33 (apparent dd, 1H, H-4', J=13.4 Hz, J=7.8 Hz), 4.11 (apparent t, 1H, H-2', J=4.8 Hz), 4.05 (s, 1H, H-4'), 3.79–3.71 (m, 2H, H-5').

EXAMPLE 16

5,6-Dichloro-2-(n-pentylamino)-1-(beta-L-ribofuranosyl)-1H-benzimidazole n-Pentylamine (5 ml) and 2-bromo-5,6-dichloro-1-(2,3,5-tri-O-acetyl-beta-L-ribofuranosyl)-1H-benzimidazole (0.6 g, 1.1 mmol) were combined with absolute ethanol (10 mL) and stirred at 80° C. for 24 h. The reaction mixture was concentrated and purified on a silica gel column (2.5 cm×16 cm, 230–400 mesh) with 1:15 methanol:dichloromethane to give 0.55 g of product with some impurities. This material was repurified on a second silica gel column (2.5 cm×16 cm, 230–400 mesh) with 1:20 methanol:dichloromethane to give an off-white solid (0.40 g, 0.99 mmol, 87%) m.p. 102–103° C.; $[a]^{20}_D$=(-) 22.0 (c=0.5 DMF).

Anal. Calcd. for $C_{17}H_{23}N_3O_4Cl_2$: C, 50.50; H, 5.73; N. 10.40. Found: C, 50.25; H, 5.85; N, 10.26.

EXAMPLE 17

2-((5,6-Dichloro-1-(beta-L-ribofuranosyl)-1H-benzimidazol-2-yl)amino)acetonitrile Amino acetonitrile hydrochloride (1.2 g, 13 mmol), triethylamine (5 mL), and 2-bromo-5,6-dichloro-1-(2,3,5-tri-O-acetyl-beta-L-ribofuranosyl)-1H-benzimidazole (0.6 g, 1.1 mmol) were combined with absolute ethanol (40 mL) and stirred at 80° C. for 3 days. The reaction mixture was concentrated and the residue was diluted with ethyl acetate (150 mL) and extracted with 10% sodium bicarbonate (25 mL) then with water (2×25 mL). The ethyl acetate layer was dried ($Na_2SO_4$) decanted and concentrated to a brown oil (0.67 g) and purified on a silica gel column (2.5 cm×18 cm, 230–400 mesh) with 1:15 methanol:dichloromethane. The two main products off the column were 2-bromo-5,6-dichloro-1-(5-O-acetyl-beta-L-ribofuranosyl)-1H-benzimidazole (0.32 g) and 2-bromo-5,6-dichloro-1-(beta-L-ribofuranosyl)-1H-benzimidazole (0.14 g). A lower $R_f$ material (0.19 g) was also isolated and further purified on a chromatotron fitted with a 2 mm rotor using 1:20 methanol:dichloromethane to give an off white solid (0.024 g, 0.06 mmol, 5%); MS (AP-): m/z (rel. intensity) 371 (80, M-2); $^1$H NMR (DMSO-$d_6$) d 7.87 (t, 1H, NH, J=5.9 Hz), 7.83 (s, 1H, Ar—H), 7.52 (s, 1H, Ar—H), 5.74 (d, 1H, H-1', J=7.6 Hz), 5.68 (t, 1H, OH, J=4.1 Hz), 5.32 (d, 1H, OH, J=7.1 Hz), 5.23 (d, 1H, OH, J=4.2 Hz), 4.37 (d, 2H, C$\underline{H}_2$CN, J=5.3 Hz), 4.28 (apparent dd, 1H, H-4', J=13.0 Hz, J=7.2 Hz), 4.07 (apparent t, 1H, H-3', J=3.5 Hz), 3.98 (s, 1H, H-3'), 3.73–3.63 (m, 2H, H-5').

Anal. Calcd. for $C_{14}H_{14}N_4O_4Cl_2$. 0.30 $CH_4O$. 0.15 $CH_2Cl_2$: C, 43.88; H, 3.95; N, 14.16. Found: C, 43.81; H, 3.90; N, 14.21.

EXAMPLE 18

2-(n-Butylamino)-5,6-dichloro-1-(beta-L-ribofuranosyl)-1H-benzimidazole n-Butylamine (5 mL), and 2-bromo-5,6-dichloro-1-(2,3,5-tri-O-acetyl-beta-L-ribofuranosyl)-1H-benzimidazole (0.6 g, 1.1 mmol) were combined with absolute ethanol (10 mL) and stirred at 80° C. for 18 h. The reaction mixture was concentrated and purified on a silica gel column (2.5 cm×18 cm, 230–400 mesh) with 1:9 methanol:dichloromethane. Crude product was obtained (0.73 g) which was further purified on a chromatotron, fitted with a 2 mm rotor, using 1:2 acetone:dichloromethane to give an off white solid (0.20 g, 0.51 mmol, 45%) m.p. 220–222° C.; $[a]^{20}_D$=(-) 17.2 (c=0.5 DMF).

Anal. Calcd. for $C_{16}H_{21}N_3O_4Cl_2$. 1/10 $H_2O$. ½ $C_3H_6O$: C, 49.91; H, 5.79; N, 9.98. Found: C, 49.75; H, 5.90; N, 10.16.

EXAMPLE 19

2-(sec-Butylamino)-5,6-dichloro-1-(beta-L-ribofuranosyl)-1H-benzimidazole sec-Butylamine (3 mL), and 2-bromo-5,6-dichloro-1-(2,3,5-tri-O-acetyl-beta-L-ribofuranosyl)-1H-benzimidazole (0.6 g, 1.1 mmol) were combined with absolute ethanol (10 mL) and stirred at 80° C. for 18 h. The reaction mixture was concentrated and purified on a silica gel column (2.5 cm×18 cm, 230–400 mesh) with 1:20 methanol:dichloromethane. Crude product was obtained (0.37 g) which was further purified on a chromatotron, fitted with a 2 mm rotor, using 1:20 methanol:dichloromethane to give an off white solid which was a mixture of diastereomers (0.21 g, 0.55 mmol, 48%) m.p. 121–122° C.; $[a]^{20}_D$=(-) 23.8 (c=0.5 DMF).

Anal. Calcd. for $C_{16}H_{21}N_3O_4Cl_2$. 7/10 $H_2O$: C, 47.70; H, 5.60; N, 10.43. Found: C, 47.76 H, 5.51; N, 10.16.

EXAMPLE 20

2-(Cyclobutylamino)-5,6-dichloro-1-(beta-L-ribofuranosyl)-1H-benzimidazole

Cyclobutylamine (3 mL), and 2-bromo-5,6-dichloro-1-(2,3,5-tri-O-acetyl-beta-L-ribofuranosyl)-1H-benzimidazole (0.6 g, 1.1 mmol) were combined with absolute ethanol (10 mL) and stirred at 80° C. for 24 h. The reaction mixture was concentrated and purified on a silica gel column (2.5 cm×18 cm, 230–400 mesh) with 2:1 ethyl acetate:hexanes. Crude product was obtained (0.42 g) which was further purified by multiple cyclings on a chromatotron, fitted with a 2 mm rotor, using 1:20 methanol:dichloromethane to give a white solid (0.26 g, 0.67 mmol, 59%) m.p. 220–221° C.; $[a]^{20}_D$=(-) 22.4 (c=0.5 DMF).

Anal. Calcd. for $C_{16}H_{19}N_3O_4Cl_2$: C, 49.50; H, 4.93; N, 10.82. Found: C, 49.22 H, 4.90; N, 10.61.

EXAMPLE 21

2-(Cycloheptylamino)-5,6-dichloro-1-(beta-L-ribofuranosyl)-1H-benzimidazole

Cycloheptylamine (2 mL), and 2-bromo-5,6-dichloro-1-(beta-L-ribofuranosyl)-1H-benzimidazole (0.4 g, 1.0 mmol) were combined with absolute ethanol (10 mL) and stirred at 80° C. for 24 h. The reaction mixture was concentrated and purified on a silica gel column (2.5 cm×18 cm, 230–400 mesh) with 1:20:20 methanol:ethyl acetate:hexanes to give an off white solid (0.13 g, 0.3 mmol, 30%) m.p. 137–138° C.; $[a]^{20}_D$=(-) 21.6 (c=0.5 DMF).

Anal. Calcd. for $C_{16}H_{19}N_3O_4Cl_2$. 11/10 $H_2O$: C, 50.70; H, 6.09; N, 9.33. Found: C, 50.91 H, 5.91; N, 9.13.

EXAMPLE 22

5,6-Dichloro-2-((2-(1-pyrrolidinyl)ethyl)amino)-1-(beta-L-ribofuranosyl)-1H-benzimidazole 1-(2-Aminoethyl)pyrrolidine (1.9 mL, 13.5 mmol), triethylamine (2 mL), and 2-bromo-5,6-dichloro-1-(beta-L- ribofuranosyl)-1H-benzimidazole (0.6 g, 1.1 mmol) were combined with absolute ethanol (10 mL) and stirred at 80° C. for 18 h. The reaction mixture was concentrated and purified on a silica gel column (2.5 cm×18 cm, 230–400 mesh) with 1:20 methanol:dichloromethane. The main product off the column was dissolved in deionized water neutralized and extracted into dichloromethane to give an off white solid (0.26 g, 0.6 mmol, 53%) m.p. 123–124° C.; $[a]^{20}{}_D=(-)$ 20.4 (c=0.5 DMF).

Anal. Calcd. for $C_{18}H_{24}N_4O_4Cl_2 \cdot \frac{3}{2} H_2O \cdot \frac{1}{2} C_4H_8O_2$: C, 47.82, H, 6.22; N, 11.15. Found: C, 47.79 H, 6.06; N, 10.97.

EXAMPLE 23

2-((Cyclopropylmethyl)amino)-5,6-dichloro-1-(beta-L-ribofuranosyl)-1H-benzimidazole (Aminomethyl)cyclopropene hydrochloride (1.6 g, 15 mmol), tributylamine (2 mL), and 2-bromo-5,6-dichloro-1-(beta-L-ribofuranosyl)-1H-benzimidazole (0.55 g, 1.05 mmol) were combined with absolute ethanol (10 mL) and stirred at 80° C. for 6 h. The reaction mixture was concentrated and purified on a silica gel column (2.5 cm×18 cm, 230–400 mesh) with 1:20 methanol:dichloromethane. The main product off the column was repurified on a silica gel column (2.5 cm×18 cm, 230–400 mesh) with 1:10:10 methanol:ethyl acetate:hexanes to give an off white solid (0.30 g, 0.77 mmol, 74%) m.p. 229–230° C.; $[a]^{20}{}_D=(-)$ 24.8 (c=0.5 DMF).

Anal. Calcd. for $C_{16}H_{19}N_3O_4Cl_2$: C, 49.50; H, 4.93; N, 10.83. Found: C, 49.30 H, 5.02; N, 10.66.

EXAMPLE 24

2-(tert-Butylamino)-5,6-dichloro-1-1(beta-L-ribofuranosyl)-1H-benzimidazole

A solution of 2-(tert-butylamino)-5,6-dichloro-1-(2,3,5-tri-O-acetyl-beta-L-ribofuranosyl)-1H-benzimidazole (2.0 g, 3.9 mmol) in methanol (40 mL) and ethanol (40 mL) was combined with a solution of sodium carbonate (0.61 g, 5.8 mmol) in water (10 mL). The solution was stirred at rt for 5 h, then the methanol and ethanol were removed on the rotoevaporator. The solution was then extracted between ethyl acetate (150 mL) and saturated NaCl (20 mL). The organics were concentrated and purified on a silica gel column (2.5 cm×14 cm, 230–400 mesh) with 1:20 methanol:dichloromethane to give a white solid (1.25 g, 3.2 mmol, 83%) m.p. 118–120° C.; $[a]^{20}{}_D=(-)$ 30.2 (c=0.5 DMF).

Anal. Calcd. for $C_{16}H_{21}N_3O_4Cl_2$: $\frac{2}{5}$ $H_2O$. $\frac{2}{5}$ $CH_4O$ C, 48.01; H, 5.75; N, 10.24. Found: C, 48.20; H, 5.73; N, 10.05.

EXAMPLE 25

2-(tert-Butylamino)-5,6-dichloro-1-(2,3,5-tri-O-acetyl-beta-L-ribofuranosyl)-1H-benzimidazole Anhydrous 1,2-dichloroethane (15 mL), 2-(tert-butylamino)-5,6-dichlorobenzimidazole (1.5 g, 5.84 mmol), and N,O-bistrimethylsilylacetamide (2.2 mL, 8.8 mmol) were combined and stirred at 80° C. for 30 min. Trimethylsilyl triflate (1.1 mL, 5.84 mmol) was added and the solution was stirred at 80° C. for 45 min. Solid 1,2,3,4-tetra-O-acetyl-L-ribofuranoside (L-TAR) (2.0 g, 6.42 mmol) was added and stirring was continued at 80° C. for 3 h. More L-TAR was added (0.5 g, 1.6 mmol) at this time. After 1 hr the reaction was quenched with cold saturated sodium bicarbonate (40 mL), then extracted with dichloromethane (2×150 mL). The combined organics were dried (sodium sulfate), decanted, and concentrated to give 4.0 g of a gold solid. This material was purified on a silica gel column (5 cm×16 cm, 230–400 mesh) with 1:30 methanol:dichloromethane to give an off white solid (2.21 g, 4.3 mmol, 73%); $[a]^{20}{}_D=(-)$ 28.4 (c=0.5 DMF).

Anal. Calcd. for $C_{22}H_{27}N_3O_7Cl_2$. 1 $CH_4O$ C, 50.37; H, 5.70; N, 7.66. Found: C, 50.74; H, 5.41; N, 7.28.

EXAMPLE 26

2-(tert-Butylamino)-5,6-dichloro-1H-benzimidazole 4,5-Dichlorophenylene diamine (8.0 g, 45.2 mmol) (Aldrich, Milwaukee, Wis.) was combined with tert-butyl isothiocyanate (6.3 mL, 49.7 mmol) (Aldrich, Milwaukee, Wis.) in anhydrous pyridine (100 mL). The solution was heated at 80° C. for 1 h under nitrogen. 1-cyclohexyl-3-(2-morpholinoethyl)carbodiimide metho-p-toluene-sulphonate (24.9 g, 58.8 mmol) (Fluka Chemika) was added along with anhydrous pyridine (90 mL). This solution was heated at 90° C. for 2.5 h. The pyridine was removed by rotoevaporation, and the residue was dissolved in ethyl acetate (300 μM) and extracted with water (4×100 mL). The ethyl acetate layer was treated with decolorizing carbon and washed through a silica gel filter pad (4×8 cm, 230–400 mesh) using ethyl acetate. The crude product was purifed on a silica gel column (5×16 cm, 230–400 mesh) using (1:4) ethyl acetate : hexane. Crude fractions were repurified on a second identical column using (1:3) ethyl acetate : hexane. Pure fractions from the two columns were combined to give a tan solid (3.13 g, 12.1 mmol, 27%); m.p. 219–221° C.; MS (API+): m/z (rel. intensity) 258 (100, M+1); $^1H$ NMR (DMSO-$d_6$) d 10.31 (s, 1H, NH), 7.31 (s, 2H, Ar—H), 6.61 (s, 1H, NH), 1.38 (s, 9H, t-butyl).

Anal. Calcd. for $C_{11}H_{13}N_3Cl_2$: C, 51.18; H, 5.08; N, 16.28. Found: C, 51.11; H, 5.12; N, 16.18.

EXAMPLE 27

2-Amino-5,6-dichloro-1-(beta-L-ribofuranosyl)-1H-benzimidazole

A solution of 2-amino-5,6-dichloro-1-(2,3,5-tri-O-acetyl-beta-L-ribofuranosyl)-1H-benzimidazole (1.0 g, 2.2 mmol) in methanol (17 mL) and ethanol (17 mL) was combined with a solution of sodium carbonate (0.25 g, 2.4 mmol) in water (4 mL). The solution was stirred at rt for 64 h, then the methanol and ethanol were removed on the rotoevaporator. The solution was then extracted between ethyl acetate (2×100 mL) and saturated NaCl (20 mL). The organics were concentrated and purified on a silica gel column (2.5 cm×14 cm, 230–400 mesh) with 1:10 methanol:dichloromethane to give a white solid (4.1 g, 1.24 mmol, 57%) m.p. 110–112° C.; $[a]^{20}{}_D=(-)$ 4.2 (c=0.5 DMF).

Anal. Calcd. for $C_{12}H_{13}N_3O_4Cl_2$. $\frac{3}{5}$ $H_2O$. $\frac{2}{5}$ $CH_4O$: C, 41.63; H, 4.45; N, 11.74. Found: C, 41.47; H, 4.27; N, 11.58.

EXAMPLE 28

2-Amino-5,6-dichloro-1-(2,3,5-tri-O-acetyl-beta-L-ribofuranosyl)-1H-benzimidazole Anhydrous 1,2-dichloroethane (100 mL), 2-amino-5,6-dichloro-benzimidazole (10 g, 49.5 mmol) (synthesized by the method of Homer and Henry J. Med. Chem. 1968, 11, 946–949), and N,O-bistrimethylsilylacetamide (18.3 mL, 74.2 mmol) were combined and stirred at 80° C. for 30 min. all the solids dissolved. Trimethylsilyl triflate (9.3 mL, 48.3 mmol) was added and the solution was stirred at 80° C. for 20 min. Solid 1,2,3,4-tetra-O-acetyl-L-ribofuranoside, (L-TAR), (17.3 g, 54.4 mmol), was added in four portions over a period of 3 h while stirring was continued at 80° C. Fortyfive minutes after the last addition, the reaction was quenched with cold saturated sodium bicarbonate (100 mL), then extracted with dichloromethane (200 mL). The combined organics were dried (sodium sulfate), decanted, and concentrated to give 24.8 g of a thick red oil. This material was purified on a silica gel column (5×20 cm, 230–400 mesh) with 1:40 methanol:dichloromethane. NMR showed high $R_f$ product from the column contained a trimethylsilyl group. These fractions were reacted with tetrabutyl ammonium fluoride in THF for 24 h, and filtered through a silica gel filter pad with 1:10 methanol : dichloromethane.

All product containing fractions were combined and repurified on a silica gel column (5×14 cm, 230–400 mesh) with 1:1 acetone:dichloromethane to give an off white solid (3.4 g, 7.4 mmol, 15%); $[a]^{20}_D$=(+) 48.0 (c=0.5 DMF).

Anal. Calcd. for $C_{18}H_{19}N_3O_7Cl_2$. ¼ $CH_2Cl_2$. ½ $C_3H_6O$: C, 46.46 H, 4.44; N, 8.23. Found: C, 46.59; H, 4.35; N, 8.07.

EXAMPLE 29

5,6-Dichloro-1-(beta-L-ribofuranosyl)-2-((2,2,2-trifluoroethyl)amino-1H-benzimidazole Triethylamine (2 mL), 2,2,2-trifluoroethylamine (2 mL), and 2-bromo-5,6-dichloro-1-(beta-L-ribofuranosyl)-1H-benzimidazole (0.4 g, 1.0 mmol) were combined with DMSO (10 mL) and stirred, in a sealed tube, at 80° C. for 17 days. The reaction mixture was extracted between water (30 mL) and dichloromethane (3×100 mL). The organics were concentrated and purified by multiple cyclings on a chromatotron fitted with a 2 mm rotor using 1:4 acetone:dichloromethane then 1:15 methanol:dichloromethane to give an off white solid (0.02 g, 0.05 mmol, 5%); MS (API+): m/z (rel. intensity) 416 (100, M+).

Anal. Calcd. for $C_{14}H_{14}N_3O_4FCl_2$. ½ $H_2O$. ⅕ $CH_4O$: C, 39.42; H, 4.13; N, 9.25. Found: C, 39.34; H, 3.95; N, 9.08.

EXAMPLE 30

5,6-Dichloro-1-(beta-L-ribofuranosyl)-1H-benzimidazole

A solution of 5,6-dichloro-1-(2,3,5-tri-O-acetyl-beta-L-ribofuranosyl)-1H-benzimidazole (0.43 g, 0.96 mmol) in methanol (10 mL) and ethanol (10 mL) was combined with a solution of sodium carbonate (0.15 g, 1.4 mmol) in water (2.5 mL). The solution was stirred at rt for 24 h. then the methanol and ethanol were removed on the rotoevaporator. The solution was then extracted between ethyl acetate (4×100 mL) and saturated NaCl (20 mL). The organics were concentrated to give an analytically pure white solid (0.27 g, 0.85 mmol, 88%) m.p. 209–210° C.; $[a]^{20}_D$=(+) 63 (c=0.5 DMF).

Anal. Calcd. for $C_{12}H_{12}N_2O_4Cl_2$. ⅖ $H_2O$. ¹⁄₁₀ $C_4H_8O_2$: C, 44.44; H, 4.09; N, 8.36. Found: C, 44.49; H, 3.91; N, 8.14.

EXAMPLE 31

5,6-Dichloro-1-(2,3,5-tri-O-acetyl-beta-L-ribofuranosyl)-1H-benzimidazole

Anhydrous acetonitrile (20 mL), 5,6-dichlorobenzimidazole (EMS-Dottikon AG) (0.59 g, 3.1 mmol), and N,O-bistrimethylsilylacetamide (0.77 mL, 3.1 mmol) were combined and stirred at 80° C. for 30 min. All the solids dissolved. Trimethylsilyl triflate (0.75 mL, 3.9 mmol) was added and the solution was stirred at rt for 15 min during which time a large amount of solid formed. Solid 1,2,3,4-tetra-O-acetyl-L-ribofuranoside, (L-TAR), (1.0 g, 3.1 mmol), was added then the solution was warmed to 80° C. All the solids dissolved. After 1.5 h the reaction mixture was quenched with cold saturated sodium bicarbonate (10 mL), then extracted with dichloromethane (100 mL). The organics were dried (sodium sulfate), decanted, and concentrated to give 1.7g of a yellow oil. This material was purified on a silica gel column (2.5×18 cm, 230–400 mesh) with 1:40 methanol:dichloromethane to give 1.37 g of a partially pure product. A second silica gel column (2.5×16 cm, 230–400 mesh) with 2:3 hexane:ethyl acetate gave pure product as a white solid. (0.8 g, 1.78 mmol, 57%); $[a]^{20}_D$=(+) 46.8 (c=0.5 DMF).

Anal. Calcd. for $C_{18}H_{18}N_2O_7Cl_2$: C, 48.56 H,4.07; N, 6.29. Found: C, 48.45; H, 4.11; N, 6.19.

EXAMPLE 32

2-Acetamido-5,6-dichloro-1-(beta-L-ribofuranosyl)-1H-benzimidazole

A solution of 2-acetamido-5,6-dichloro-1-(2,3,5-tri-O-acetyl-beta-L-ribofuranosyl)-1H-benzimidazole (0.35 g, 0.75 mmol) in methanol (8 mL) and ethanol (8 mL) was combined with a solution of sodium carbonate (0.12 g, 1.1 mmol) in water (2 mL). The solution was stirred at rt for 24 h, then the methanol and ethanol were removed on the rotoevaporator. The solution was then extracted between ethyl acetate (2×150 mL) and saturated NaCl (20 mL). The organics were concentrated and purified by multiple cyclings on a chromatotron, fitted with a 2 mm rotor, using 1:10 methanol:dichloromethane to give a white solid (0.067 g, 0.18 mmol, 23%); This material was identified by $^1H$ NMR, MS and HPLC, it contained about 7% of 2-amino-5,6-dichloro-beta-L-ribofuranosyl-1H-benzimidazole by $^1H$ NMR. HPLC showed two small (~5%) impurities.

EXAMPLE 33

5,6-Dichloro-2-(methylamino)-1-(beta-L-ribofuranosyl)-1H-benzimidazole

Methylamine hydrochloride (3.0 g, 45 mmol), triethylamine (3 mL), and 2-bromo-5,6-dichloro-1-(2,3,5-tri-O-acetyl-beta-L-ribofuranosyl)-1H-benzimidazole (0.6 g, 1.1 mmol) were combined with absolute ethanol (25 mL) and stirred at 80° C. for 24 h. The reaction mixture was separated between saturated sodium bicarbonate (50 mL) and ethyl acetate (150 mL). The organic layer was dried with sodium sulfate, concentrated and absorbed onto silica gel (15 g). This material was dry loaded onto a silica gel column (5 cm×10 cm, 230–400 mesh) with 1:10 methanol:dichloromethane. The main product came off the column as a white solid (0.22 g, 0.62 mmol, 54%) m.p. 238–240° C.; $[a]^{20}_D$= (−) 15.2 (c=0.5 DMF).

Anal. Calcd. for $C_{13}H_{15}N_3O_4Cl_2$. ½ $CH_4O$: C, 44.52; H, 4.70; N, 11.54. Found: C, 44.43; H, 4.58; N, 11.36.

EXAMPLE 34

5,6-Dichloro-2-(ethylamino)-1-(beta-L-ribofuranosyl)-1H-benzimidazole

Ethylamine hydrochloride (3.7 g, 46 mmol), triethylamine (7 mL), and 2-bromo-5,6-dichloro-1-(2,3,5-tri-O-acetyl-beta-L-ribofuranosyl)-1H-benzimidazole (0.60 g, 1.1 mmol)

were combined with absolute ethanol (20 mL) and stirred at 80° C. for 24 h. The reaction mixture was separated between saturated sodium bicarbonate (2×50 mL) and ethyl acetate (200 mL). The organics were dried with sodium sulfate, concentrated, and purified on a silica gel column (2.5×18 cm, 230–400 mesh) with 1:20 methanol:dichloromethane. The main product off the column was a white solid (0.30 g, 0.96 mmol, 87%) m.p. 155–157° C.; $[\alpha]^{20}_D$=(−) 20.6 (c=0.5 DMF).

Anal. Calcd. for $C_{14}H_{17}N_3O_4Cl_2$. ½ $H_2O$: C, 45.30; H, 4.89; N, 11.32. Found: C, 45.44; H, 4.78; N, 11.18.

EXAMPLE 35

2-Cyclopropylamino-5,6-dichloro-1-(alpha-L-ribofuranosyl)-1H-benzimidazole

Cyclopropylamine (10 mL) and 2-bromo-5,6-dichloro-1-(2,3,5-tri-O-acetyl-alpha-L-ribofuranosyl)-1H-benzimidazole (0.60 g, 1.1 mmol) (obtained as a minor product from the synthesis of the beta anomer, see Example 1) were combined with absolute ethanol (50 mL) and stirred at 80° C. for 24 h. The reaction mixture was concentrated and purified on a silica gel column (2.5×16 cm, 230–400 mesh) with 1:9 methanol:dichloromethane to give 0.25 g of crude product. This material was further purified by multiple cycles on a chromatotron, fitted with a 1 mm silica gel rotor, with 1:15 methanol: dichloromethane to give a white solid (0.060 g, 0.14 mmol, 14%); m.p. 140–141° C.; $[\alpha]^{20}_D$=(−) 51.8 (c=0.5 DMF); UV $l_{max}$ (e): pH 7.0: 303 nm (10,600), 274 (1,700); 0.1 N NaOH: 304 nm (10,800), 275 (2,400); MS (CI): m/z (rel. intensity) 374 (29.7, M+1); $^1$H NMR (DMSO-$d_6$) d 7.48 (s, 1H, Ar—H), 7.38 (s, 1H, Ar—H), 7.08 (br. s, 1H, NH), 5.86 (d, 1H, H-1', J=3.4 Hz), 5.50 (d, 1H, OH, J=4.5 Hz), 5.22 (d, 1H, OH, J=7.1 Hz), 4.84 (t, 1H, OH, J=5.7 Hz), 4.15 (dd, 1H, H-2', J=7.9 Hz, J=4 Hz), 7.9 Hz, J=4 Hz), 4.10 (dd, 1H, H-3', J=7.3 Hz, J=4.5 Hz), 4.05–4.01 (m, 1H, H-4'), 3.66–3.61 (m, 1H, H-5'), 3.47–3.41 (m, 1H, H-5''), 2.74–2.71 (dd, 1H, cyclopropyl-CH, J=6.7 Hz, J=3.3 Hz), 0.69 (d, 2H, J=6.9 Hz, cyclopropyl-$CH_2$), 0.51–0.45 (m, 2H, cyclopropyl-$CH_2$).

Anal. Calcd. for $C_{15}H_{17}N_3O_4Cl_2$. 0.60 $CH_4O$. 0.2 $CH_2Cl_2$: C, 46.24; H, 4.86; N, 10.24. Found: C, 46.13; H, 4.83; N, 10.28.

EXAMPLE 36

5,6-Dichloro-2-(isopropylamino)-1-(alpha-L-ribofuranosyl)-1H-benzimidazole

Isopropylamine (10 mL) and 2-bromo-5,6-dichloro-1-(2,3,5-tri-O-acetyl-alpha-L-ribofuranosyl)-1H-benzimidazole (0.60 g, 1.14 mmol) (obtained as a minor product from the synthesis of the beta anomer) were combined with absolute ethanol (10 mL) and stirred at 80° C. for 24 h. The reaction mixture was concentrated and purified on a silica gel column (2.5×18 cm, 230–400 mesh) with 1:15 methanol:dichloromethane to give 0.39 g of crude product. This material was further purified on a chromatotron, fitted with a 1 mm silica gel rotor, with 1:2 acetone: dichloromethane to give a white solid (0.29 g, 0.78 mmol, 68%); m.p. 131–133° C.; $[\alpha]^{20}_D$= (−) 41.4 (c=0.5 DMF); UV $l_{max}$ (e): pH 7.0: 304 nm (11,000), 276 (2,000); 0.1 N NaOH: 306 nm (11,500), 277 (2,500); MS (CI): m/z (rel. intensity) 376 (34.8, M+1); $^1$H NMR (DMSO-$d_6$) d 7.46 (s, 1H, Ar—H), 7.31 (s, 1H, Ar—H), 6.63 (d, 1H, NH, J=7.4 Hz), 5.94 (d, 1H, H-1', J=3.4 Hz), 5.53 (d, 1H, OH, J=4.4 Hz), 5.22 (d, 1H, OH, J=7.1 Hz), 4.86 (t, 1H, OH, J=5.7 Hz), 4.15 (dd, 1H, H-2', J=7.7 Hz, J=4.0 Hz), 4.10 (dd, 1H, H-3', J=7.3 Hz, J=4.3 Hz), 4.05–3.94 (m, 2H, isopropyl CH, H-4'), 3.69–3.63 (m, 1H, H-5'), 3.49–3.41 (m, 1H, H-5''), 1.19 (d, 3H, J=6.5 Hz, isopropyl-$CH_3$), 1.18 (m, 3H, isopropyl-$CH_3$).

Anal. Calcd. for $C_{15}H_{17}N_3O_4Cl_2$. 0.4 $CH_2Cl_2$: C, 45.09; H, 4.86; N, 10.24. Found: C, 45.10; H. 4.97; N, 10.00.

EXAMPLE 37

5,6-Dichloro-2-((2-fluoro-1-methylethylamino)-1-(beta-L-ribofuranosyl)-1H-benzimidazole Sodium carbonate (0.032 g, 0.30 mmol) and 5,6-dichloro-2-(2-fluoroisopropylamino)-1-(2,3,5-tri-O-acetyl-beta-L-ribofuranosyl)-1H-benzimidazole (0.10 g, 0.20 mmol) were combined with water (1 mL), methanol (2.5 mL) and ethanol (2.5 mL) and stirred at rt for 3 h. The solution was concentrated to remove most of the methanol and ethanol and then combined with ethyl acetate (75 mL). This solution was extracted with sat'd NaCl (2×5 mL). The organics were dried ($Na_2SO_4$), decanted, and concentrated. Purification of the residue on a chromatrotron, fitted with a 1 mm rotor, with 1:10 methanol : $CH_2Cl_2$ gave a white solid (0.066 g, 0.17 mmol, 84%); $[\alpha]^{20}_D$=(−) 24.8 (c=0.5 DMF); MS (AP+): m/z (rel. intensity) 394 (98, M+); $^1$H NMR (DMSO-$d_6$) d 7.64(s, 1H, Ar—H), 7.37 (s, 1H, Ar—H), 7.13 (d, 0.5H, NH, J=7.9 Hz), 7.07 (d, 0.5H, NH, J=7.6 Hz), 5.76 (d, 1H, J=7.9 Hz, H-1'), 5.69 (m, 1H, OH), 5.31–5.23 (m, 2H, OH), 4.51–4.45 (m, 1H, $CH_2F$), 4.35–4.32 (m, 1H, $CH_2F$), 4.29–4.17 (m, 2H, H-2' and H-3'), 4.06–3.97 (m, 1H, NHC$\underline{H}$), 3.97 (br. s, 1H, H-4'), 3.70–3.31 (m, 2H, H-5'), 1.22–1.18 (m, 3H, $CH(CH_3)$).

Anal. Calcd. for $C_{15}H_{18}N_3O_4Cl_2F$. 0.40 $H_2O$: C, 44.88; H, 4.72; N, 10.47. Found: C, 44.98; H, 4.76; N, 10.46.

EXAMPLE 38

5,6-Dichloro-2-((2-fluoro-1-methylethylamino)-1-(2,3,5-tri-O-acetyl-beta-L-ribofuranosyl)-1H-benzimidazole Fluoroacetone (5 g) and 5,6-dichloro-2-amino-1-(2,3,5-tri-O-acetyl-beta-L-ribofuranosyl)-1H-benzimidazole (0.38 g, 0.82 mmol) were combined with tosic acid (0.050 g, 0.26 mmol) and stirred at reflux in a flask fitted with a Dean Stark trap. After four hours sodium cyanoborohydride (0.16 g, 2.4 mmol) was added and reflux was continued for six hours. The solution was diluted with ethyl acetate (200 mL) and washed with sat'd NaCl (2×50 mL) and water (50 mL). The organics were dried ($Na_2SO_4$), decanted, and concentrated. The crude product was purified on a silica gel column (230–400 mesh, 2.5×18 cm) with 1:25 methanol: $CH_2Cl_2$ gave 0.19 g of crude product. This material was further purified on a chromatotron (2 mm rotor) with 1:1 ethyl acetate hexanes to give a light yellow solid (0.10 g, 0.20 mmol, 24%); MS (API+; m/z (rel. intensity) 520 (62.63, M+); $^1$H NMR (DMSO-$d_6$) d 7.66(s, 1H, Ar—H), 7.51 (s, 1H, Ar—H), 7.30 (d, 1H, NH, J=7.6 Hz), 6.25 (d, 1H, H-1', J=7.5 Hz), 5.31–5.23 (m, 1H, H-2'), 5.48–5.44 (m, 1H, H-3'), 4.63–4.26 (m, 6H, $CH_2F$, CH, H-4' and 5'), 2.21 (s, 3H, OAc), 2.19 (s, 3H, OAc), 2.02 (s,3H, OAc), 1.24 (d, 3H, CH(C$\underline{H}_3$), J=7.5 Hz).

Anal. Calcd. for $C_{21}H_{24}N_3O_7Cl_2F$: C, 48.47; H, 4.65; N, 8.08. Found: C, 48.60; H, 4.73; N, 7.94.

EXAMPLE 39

5,6-Dichloro-2-(isopropylamino)-1H-benzimidazole 5,6-Dichloro-1,2-phenylenediamine (0.61 g, 3.4 mmol), and isopropyl isothiocyanate (0.39 g, 3.8 mmol) were combined in anhydrous pyridine (10 mL) and were heated to 80° C. for 15 min. Dicyclohexylcarbodiimide (1.06 g, 5.14 mmol) was then added and the resulting mixture was allowed to stir at 100° C. for 5 h. Toluene (30 mL) was added and the mixture was concentrated by rotary evaporation leaving a brown residue. The product was further purified by silica gel chromatography using 6.5:3:0.5 ethyl acetate/hexane/triethylamine to afford a gummy solid which was recrystallised from acetonitrile to give 0.46 g (60%) of a tan solid; m.p. 218–220° C. Anal. Calcd for $C_{10}H_{11}Cl_2N_3$: C, 49.20; H, 4.54; N, 17.21. Found: C, 49.31; H, 4.59; N, 17.33.

General Procedure I

Synthesis of 2-(alkylamino)-1H-benzimidazoles Using 1-cyclohexyl-3-(2-morpholinoethyl)carbodiimide metho-p-toluenesulphonate as Desulphurising Agent.

The appropriate 1,2-phenylenediamine is combined with the appropriate isothiocyanate (1.0–1.25 mmol/mmol of diamine) and anhydrous pyridine (3–5 mL/mmol of diamine). The resulting mixture is heated to 80° C. for 30 min, then 1-cyclohexyl-3-(2-morpholinoethyl)carbodiimide metho-p-toluenesulfonate (1.1–1.35 mL/mmol of diamine) is added as a solid in one portion. The resulting mixture is allowed to stir at 80–90° C. for 3–20 h, after which time it is allowed to cool to room temperature. The remainder of the procedure is the same as detailed above, except that the product is purified either by silica gel chromatography or by recrystallization from either acetonitrile or 1,4-dioxane.

5,6-Dichloro-2-(isopropylamino)-1H-benzimidazole 5,6-Dichloro-1,2-phenylenediamine (200.0 g, 1.13 mol), isopropyl isothiocyanate (122.0 g, 1.21 mol), 1-cyclohexyl-3-(2-morpholinoethyl)carbodiimide metho-p-toluenesulfonate (622.0 g, 1.47 mol) and pyridine (4 L) were used according to general procedure I. The product was recrystallized from acetonitrile to give 184 g (67%) of a brown solid. Analytical data were consistent with those reported above.

2-(Cyclopropylamino)-5,6-dichloro-1H-benzimidazole 4,5-Dichloro-1,2-phenylenediamine (6.04 g, 34.1 mmol), cyclopropyl isothiocyanate (3.69 g, 37.2 mmol), 1-cyclohexyl-3-(2-morpholinoethyl)carbodiimide metho-p-toluenesulfonate (20.1 g, 47.4 mmol) and pyridine (135 mL) were used according to general procedure I. The product was recrystallized from acetonitrile to afford 5.82 g (70%) of a yellow solid; m.p. 223–225° C. Anal. Calcd for $C_{10}H_9Cl_2N_3$: C, 49.61; H, 3.75; N, 17.36. Found: C, 49.53; H, 3.78; N, 17.12.

General Procedure II

Coupling of 2-(alkylamino)-1H-benzimidazole with 1,2,3,5-tri-O-acetyl-L-ribofuranose The appropriate 2-(alkylamino)-1H-benzimidazole was combined with 1,2-dichloroethane (2–3 mL/mmol of benzimidazole) and N,O-bis(trimethylsilyl)acetamide (1–1.25 mmol/mmol of benzimidazole) and the resulting mixture was heated to 80° C. for 30 min. Trimethylsilyl trifluoromethanesulfonate (0.5–0.7 mmol/mmol of benzimidazole) was added and the mixture was allowed to stir at 80° C. for an additional 15 min, after which time 1,2,3,5-tetra-O-acetyl-L-ribofuranose (1–1.25 mmol/mmol of benzimidazole) was added as a solid in one portion. The resulting mixture was allowed to stir at 80° C. for 2–20 h, after which time it was allowed to cool to room temperature. It was then diluted with 5% aqueous sodium bicarbonate (10 mL/mmol of benzimidazole) and dichloromethane (3–5 mL/mmol of benzimidazole) and the two-phase mixture was stirred at room temperature for 30 min. The organic layer was collected and the aqueous layer was back-extracted with an additional portion of dichloromethane (3–5 mL/mmol of benzimidazole) and the combined organic layers were dried over magnesium sulfate, filtered and the solvents were removed under reduced pressure using a rotary evaporator. The products were further purified by silica gel chromatography.

5,6-Dichloro-2-(isopropylamino)-1-(2,3,5-tri-O-acetyl-beta-L-ribofuranosyl)-1H-benzimidazole 5,6-Dichloro-2-(isopropylamino)-1H-benzimidazole (25.0 g, 102 mmol), N,O-bis(trimethylsilyl)acetamide (25.9 mL, 21.3 g, 105 mmol, 1.03 eq.), 1,2-dichloroethane (300 mL), trimethylsilyl trifluoromethanesulfonate (12.8 mL, 14.7 g, 66.2 mmol, 0.65 eq.) and 1,2,3,5-tri-O-acetyl-L-ribofuranose (34.1 g, 107 mmol, 1.05 eq.) were used according to general procedure II. Silica gel chromatography using 35:1 dichloromethane/methanol afforded 39.6 g (77%) of a yellow foam. MS (CI): m/z 501 (M+1).

General Procedure III

Deprotection of 2-(alkylamino)-1-(2,3,5-tri-O-acetyl-beta-L-ribofuranosyl)-1H-benzimidazole The appropriate 2-(alkylamino)-1-(2,3,5-tri-O-acetyl-beta-L-ribofuranosyl)-1H-benzimidazole was dissolved in ethanol (4–5 mL/mmol of triacetate). Into a separate flask were placed sodium carbonate (1.0–1.3 mmol/mmol of triacetate), water (1–2 mL/mmol of triacetate), and methanol (3 mL/mmol of triacetate). The sodium carbonate suspension was added to the ethanolic solution of the triacetate at room temperature and in one portion. The resulting mixture was allowed to stir at room temperature for 18 h. The mixture was then diluted with ethyl acetate (25 mL/mmol of triacetate). The organic layer was collected and was washed with saturated aqueous brine (100 mL/mmol of triacetate), dried over magnesium sulfate. filtered, and the solvents were removed by rotary evaporation. The products were further purified by silica gel chromatography.

5,6-Dichloro-2-(isopropylamino)-1-(beta-L-ribofuranosyl)-1H-benzimidazole 5,6-Dichloro-2-(isopropylamino)-1-(2,3,5-tri-O-acetyl-beta-L-ribofuranosyl)-1H-benzimidazole (7.50 g, 14.93 mmol), sodium carbonate (1.72 g, 16.23 mmol), water (29 mL), methanol (100 mL) and ethanol (100 mL) were used according to general procedure III. The product was purified by silica gel chromatography using 55:45 dichloromethanel-methanol to afford 4.72 g (84%) of a white foam. Analytical data were consistent with the assigned structure.

EXAMPLE 40

Human Cytomegalovirus (HCMV) Assay

HCMV strain AD169 was grown on monolayers of human embryonic lung cells ($MRC_5$ cells) in 96 well plates. After infection of the cells at a ratio of approximately 0.01 infectious virus particles per cell, the compounds to be tested were added to selected wells at six different concentrations, each in triplicate. The same concentrations of compound were also applied to wells containing monolayers of uninfected cells in order to assess compound cytotoxicity. The plates were incubated for 5 days, and the minimum cytotoxic dose was estimated from microscopic examination. The $IC_{50}$ for antiviral effect was estimated from measurements of HCMV DNA in each well by blotting and quantitive specific DNA hybridization, similar to the method of Gadler. (Antimicrob. Agents Chemother. 1983, 24, 370–374).

| Example | HCMV IC50 | MRC5 tox CC50 |
|---|---|---|
| Example 3 | 0.06–0.23 $\mu$M | 30 $\mu$M |
| Example 4 | 0.91–2.5 $\mu$M | 100 $\mu$M |
| Example 5 | 0.03–0.05 $\mu$M | 100 $\mu$M |
| Example 10 | 1.1–1.3 $\mu$M | 100 $\mu$M |
| Example 8 | 41 $\mu$M | 100 $\mu$M |
| Example 12 | 3.5–5.8 $\mu$M | 100 $\mu$M |
| Example 34 | 0.75–0.85 $\mu$M | 100 $\mu$M |

EXAMPLE 41

Tablet Formulations

The following formulations A and B were prepared by wet granulation of the ingredients with a solution of povidone, followed by addition of magnesium stearate and compression.

Formulation A

|  | mg/tablet | mg/tablet |
|---|---|---|
| (a) Active ingredient | 250 | 250 |
| (b) Lactose B.P. | 210 | 26 |
| (c) Povidone B.P. | 15 | 9 |
| (d) Sodium Starch Glycollate | 20 | 12 |
| (e) Magnesium Stearate | 5 | 3 |
|  | 500 | 300 |

Fomulation B

|  | mg/tablet | mg/tablet |
|---|---|---|
| (a) Active ingredient | 250 | 250 |
| (b) Lactose | 150 | — |
| (c) Avicel PH 101 | 60 | 26 |
| (d) Povidone B.P. | 15 | 9 |
| (e) Sodium Starch Glycollate | 20 | 12 |
| (f) Magnesium Stearate | 5 | 3 |
|  | 500 | 300 |

Formulation C

|  | mg/tablet |
|---|---|
| Active ingredient | 100 |
| Lactose | 200 |
| Starch | 50 |
| Povidone | 5 |
| Magnesium sterate | 359 |

The following formulations, D and E, were prepared by direct compression of the admixed ingredients. The loctose used in formulation E was of the direct compression type (Dairy Crest—"Zeparox").

Formulation D

|  | mg/tablet |
|---|---|
| Active Ingredient | 250 |
| Pregelatinised Starch NF15 | 150 |
|  | 400 |

Formulation E

|  | mg/tablet |
|---|---|
| Active Ingredient | 250 |
| Lactose | 150 |
| Avicel | 100 |
|  | 500 |

Formulation F (Controlled Release Formulation)

The formulation was prepared by wet granulation of the ingredients (below) with a solution of povidone followed by the addition of magnesium stearate and compression.

|  | mg/tablet |
|---|---|
| (a) Active Ingredient | 500 |
| (b) Hydroxypropylmethylcellulose (Methocel K4M Premium) | 112 |
| (c) Lactose B.P. | 53 |
| (d) Povidone B.P.C. | 28 |
| (e) Magnesium Stearate | 7 |
|  | 700 |

EXAMPLE 42

Capsule Formulations

Formulation A

A capsule formulation was prepared by admixing the ingredients of Formulation D in Example 1 above and filling into a two-part hard gelatin capsule. Formulation B (infra) was prepared in a similar manner.

Formulation B

|  | mg/tablet |
|---|---|
| (a) Active ingredient | 250 |
| (b) Lactose B.P. | 143 |
| (c) Sodium Starch Glycollate | 25 |
| (d) Magnesium Stearate | 2 |
|  | 420 |

| Formulation C | |
|---|---|
| | mg/tablet |
| (a) Active ingredient | 250 |
| (b) Macrogol 4000 BP | 350 |
| | 600 |

Capsules were prepared by melting the macrogol 4000 BP, dispersing the active ingredient in the melt and filling the melt into a two-part hard gelatin capsule.

| Formulation D | |
|---|---|
| | mg/tablet |
| Active ingredient | 250 |
| Lecithin | 100 |
| Arachis Oil | 100 |
| | 450 |

Capsules were prepared by dispersing the active ingredient in the lecithin and arachis oil and filling the dispersion into soft, elastic gelatin capsules.

Formulation E (Controlled Release Capsuler)

The following controlled release capsule formulation was prepared by extruding ingredients a, b and c using an extruder, followed by spheronisation of the extrudate and drying. The dried pellets were then coated with release-controlling membrane (d) and filled into a two-piece, hard gelatin capsule.

| | mg/tablet |
|---|---|
| (a) Active Ingredient | 250 |
| (b) Microcrystalline Cellulose | 125 |
| (c) Lactose BP | 125 |
| (d) Ethyl Cellulose | 13 |
| | 513 |

EXAMPLE 43

Injectable Formulation

| Formulation A | |
|---|---|
| Active ingredient | 0.200 g |
| Hydrochloric acid solution, 0.1 M | q.s. to pH 4.0 to 7.0 |
| Sodium hydroxide Solution, 0.1 M | q.s. to pH 4.0 to 7.0 |
| Sterile water | q.s. to 10 ml |

The active ingredient was dissolved in most of the water (35°–40° C.) and the pH adjusted to between 4.0 and 7.0 with the hydrochloric acid or the sodium hydroxide as appropriate. The batch was then made up to volume with the water and filtered through a sterile micropore filter into a sterile 10 ml amber glass vial (type 1) and sealed with sterile closures and overseals.

| Formulation B | |
|---|---|
| Active ingredient | 0.125 g |
| Sterile, pyrogen-free, pH7 phosphate buffer, | q.s. to 25 ml |

EXAMPLE 44

| Intramuscular injection | |
|---|---|
| Active ingredient | 0.20 g |
| Benzyl Alcohol | 0.10 g |
| Glycofurol | 1.45 g |
| Water for Injection | q.s. to 3.00 ml |

The active ingredient was dissolved in the glycofurol. The benzyl alcohol was then added and dissolved, and water added to 3 ml. The mixture was then filtered through a sterile micropore filter and sealed in sterile 3 ml amber glass vials (type 1).

EXAMPLE 45

| Syrup | |
|---|---|
| Active ingredient | 0.2500 g |
| Sorbitol Solution | 1.5000 g |
| Glycerol | 2.0000 g |
| Sodium Benzoate | 0.0050 g |
| Flavour, Peach 17.42.3169 | 0.0125 ml |
| Purified Water | q.s. to 5.0000 ml |

The active ingredient was dissolved in a mixture of the glycerol and most of the purified water. An aqueous solution of the sodium benzoate was then added to the solution, followed by addition of the sorbitol solution and finally the flavour. The volume was made up with purified water and mixed well.

EXAMPLE 46

| Suppository | |
|---|---|
| | mg/suppository |
| Active Ingredient (63 lm)* | 250 |
| Hard Fat, BP (Witepsol H15 - Dynamit Nobel) | 1770 |
| | 2020 |

One-fifth of the Witepsol H15 was melted in a steam-jacketed pan at 45° C. maximum. The active ingredient was sifted through a 100 l m sieve and added to the molten base with mixing, using a silverson fitted with a cutting head, until a smooth dispersion was achieved. Maintaining the mixture at 45° C., the remaining Witepsol H15 was added to the suspension and stirred to ensure a homogeneous mix. The entire suspension was passed through a 250 l m stainless steel screen and, with continuous stirring, was allowed to cool to 40° C. At a temperature of 38° C. to 40° C., 2.02 g of the mixture was filled into suitable, 2 ml plastic moulds. The suppositories were allowed to cool to room temperature.

EXAMPLE 47

| Pessaries | |
|---|---|
| | mg/pessary |
| Active ingredient (631 m) | 250 |
| Anhydrate Dextrose | 380 |
| Potato Starch | 363 |
| Magnesium Stearate | 7 |
| | 1000 |

The above ingredients were mixed directly and pessaries prepared by direct compression of the resulting mixture.

We claim:

1. A compound of formula (I)

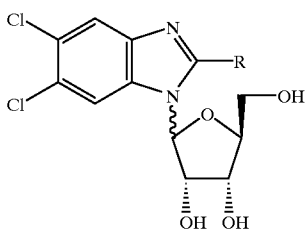

(I)

wherein R represents hydrogen, a halo atom, —NR$^1$R$^2$ where R$^1$ and R$^2$, which may be the same or different, are each independently selected from hydrogen, C$_{1-6}$ alkyl, cyanoC$_{1-6}$ alkyl, hydroxyC$_{1-6}$alkyl, haloC$_{1-6}$ alkyl, C$_{3-7}$cycloalkyl, C$_{1-6}$alkylC$_{3-7}$cycloalkyl, C$_{2-6}$ alkenyl, C$_{3-7}$cycloalkylC$_{1-6}$alkyl, C$_{2-6}$alkynyl, aryl, arylC$_{1-6}$alkyl, heterocyclicC$_{1-6}$ alkyl, —COC$_{1-6}$alkyl or R$^1$ and R$^2$ together with the N atom to which they are attached form a 3, 4, 5 or 6 membered heterocyclic ring or a pharmaceutically acceptable derivatives thereof.

2. A compound according to claim 1, in the form of a β-anomer.

3. A compound according to claim 1, in the form of an α-anomer.

4. 5,6-dichloro-2-isopropylamino-1-(β-L-ribofaranosyl)-1H-benzimidazole.

5. A compound according to claim 1 wherein R represents —NR$^1$R$^2$ wherein R$^1$ represents hydrogen and R$^2$ is selected from C$_{1-6}$alkyl, C$_{3-7}$cycloalkyl and haloC$_{1-6}$alkyl or a pharmaceutically acceptable derivatives thereof.

6. A compound according to claim 1 wherein R represents isopropylamino, isobutylamino, sec-butylamino, cyclopropylamino, cyclopentylamino or 2-fluoro-1-methylethylamino or a pharmaceutically acceptable derivatives thereof.

7. A compound according to claim 1 selected from 5,6-dichloro-2-isopropylamino-1-(β-L-ribofuranosyl)-1H-benzimidazole, 2-cyclopropylamino-5,6-dichloro-1-(β-L-ribofuranosyl)-1H-benzimidazole and 5,6-dichloro-2-((2-fluoro-1-methyl-ethylamino)-1-(β-L-ribofuranosyl)-1H-benzimidazole or a pharmaceutically acceptable derivative thereof.

8. A compound of formula (II)

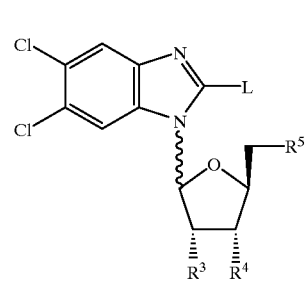

(II)

wherein L is hydrogen or a suitable leaving atom or group and R$^3$, R$^4$ and R$^5$ are each a hydroxy or a protected hydroxy group.

9. A compound according to claim 4 wherein L is hydrogen or a halo atom and R$^3$, R$^4$ and R$^5$ are each a hydroxy or a protected hydroxy group.

10. A compound according to claim 9 wherein R$^3$, R$^4$, and R$^5$ are each OC(O)CH$_3$.

11. 2-bromo-5,6-dichloro-1-(2,3,5-tri-O-acetyl-β-L-ribofuranosyl)-1H-benzimidazole.

12. 2-bromo-5,6-dichloro-1-(β-L-ribofuranosyl)-1H-benzimidazole.

13. A compound of formula (Ib)

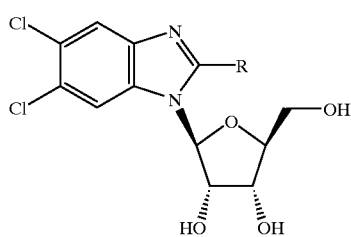

(Ib)

wherein R represents a halo atom or —NR$^1$R$^2$ wherein R$^1$ represents hydrogen and R$^2$ is selected from C$_{1-6}$alkyl, hydroxyC$_{1-6}$alkyl, C$_{3-7}$cycloalkyl, C$_{1-6}$alkylC$_{3-7}$cylcoalkyl, C$_{2-6}$alkenyl, C$_{2-6}$alkynyl, aryl, arylalkyl, or R$^1$ and R$^2$, which may be the same or different, are both C$_{1-6}$alkyl, or R$^1$ and R$^2$ together with the N atom to which they are attached form a 3, 4, 5, or 6 membered heterocyclic ring or a pharmaceutically acceptable derivative thereof.

14. A pharmaceutical formulation comprising a compound of formula (I) as defined in claim 1 or a pharmaceutically acceptable derivative thereof, together with pharmaceutically acceptable carrier therefore.

15. A pharmaceutically acceptable derivative of a compound according to claim 1.

16. A derivative according to claim 15 in the form of a salt.

17. A derivative according to claim 15 in the form of an ester.

18. A derivative according to claim 16 wherein the salt is selected from salts of organic carboxylic acids, organic sulphonic acids and inorganic acids.

19. A derivative according to claim 17 wherein the ester is selected from carboxylic acid, sulphonate, amino acid, phosphonate and mono-, di- or tri-phosphate esters.

20. A pharmaceutical composition comprising an effective antiviral amount of the compound 5,6-dichloro-2-isopropylamino-1-(β-L-ribofuranosyl)-1H-benzimidazole or a pharmaceutically acceptable derivative thereof and a pharmaceutically acceptable carrier therefor.

21. A pharmaceutical composition according to claim 20 in the form of a tablet or capsule.

22. A pharmaceutical composition according to claim 21 wherein the tablet or capsule contains 5 to 1000 mg of 5,6-dichloro-2-isopropylamino-1-(β-L-ribofuranosyl)-1H-benzimidazole or a pharmaceutically acceptable derivative thereof.

23. A pharmaceutical composition according to claim 20 in the form of a solution or suspension.

24. A method of treatment of a herpes virus infection in an infected animal which comprises treating said animal with a therapeutically effective amount of a compound as defined according to claim 1.

25. A method according to claim 24 wherein the herpes virus infection is selected from herpes simplex virus 1, herpes simplex virus 2, varicella zoster virus, cytomegalovirus (CMV), Epstein Barr virus, human herpes virus 6 and human herpes virus 7.

26. A method of treatment of a herpes virus infection in a human comprising administration to said human of an effective herpes virus infection treatment amount of the compound 5,6-dichloro-2-isopropylamino-1-(β-L-ribofuranosyl)-1H-benzimidazole.

27. The method of claim 26 wherein the herpes virus infection is CMV or Epstein Barr virus infection.

28. The method according to claim 26 wherein the administration of 5,6-dichloro-2-isopropylamino-1-(β-L-ribofuranosyl)-1H-benzimidazole is by an intravenous or intravitreal route.

29. A method of preventing the symptoms or effects of a CMV infection in a human comprising administering to said human an effective amount of the compound 5,6-dichloro-2-isopropylamino-1-(β-L-ribofuranosyl)-1H-benzimidazole.

30. A method of treatment of a CMV infection in a human, comprising administering to said human an effective CMV treatment amount of 5,6-dichloro-2-isopropylamino-1-(β-L-ribofuranosyl)-1H-benzimidazole or a pharmaceutically acceptable salt or ester thereof.

* * * * *

UNITED STATES PATENT AND TRADEMARK OFFICE
Certificate

Patent No. 6,077,832                                                  Patented: June 20, 2000

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Stanley Dawes Chamberlain, Chapel Hill, NC; Susan Mary Daluge, Chapel Hill, NC; George Walter Koszalka, Chapel Hill, NC; Leroy B. Townsend, Ann Arbor, MI; and John C. Drach, Ann Arbor, MI.

Signed and Sealed this Fifteenth Day of November 2005.

*JAMES O. WILSON*
*Supervisory Patent Examiner*
Art Unit 1623